(12) United States Patent
Valenti, Jr. et al.

(10) Patent No.: US 7,828,333 B1
(45) Date of Patent: Nov. 9, 2010

(54) LABEL SHEET WITH WRISTBAND

(75) Inventors: F. Paul Valenti, Jr., Barrington, IL (US);
Carl Opel, Carol Stream, IL (US);
Daniel Hedger, Grayslake, IL (US)

(73) Assignee: Chicago Tag & Label, Inc.,
Libertyville, IL (US)

( * ) Notice: Subject to any disclaimer, the term of this patent is extended or adjusted under 35 U.S.C. 154(b) by 0 days.

(21) Appl. No.: 12/175,736

(22) Filed: Jul. 18, 2008

(51) Int. Cl.
*B42D 15/00* (2006.01)
*A44C 5/00* (2006.01)
*A61B 5/103* (2006.01)
*A61B 5/117* (2006.01)
*G09F 3/10* (2006.01)

(52) U.S. Cl. .................. 283/108; 283/81; 283/101; 40/633; 40/675

(58) Field of Classification Search .................. 40/360, 40/633, 675; 283/81, 101, 107–111
See application file for complete search history.

(56) References Cited

U.S. PATENT DOCUMENTS

| | | | |
|---|---|---|---|
| 4,854,610 A * | 8/1989 | Kwiatek | .................. 462/2 |
| 5,653,472 A | 8/1997 | Huddleston et al. | |
| 5,933,993 A | 8/1999 | Riley | |
| 6,000,160 A | 12/1999 | Riley | |
| 6,016,618 A | 1/2000 | Attia et al. | |
| 6,067,739 A | 5/2000 | Riley | |
| 6,438,881 B1 | 8/2002 | Riley | |
| 6,836,215 B1 | 12/2004 | Laurash et al. | |
| 6,971,200 B2 | 12/2005 | Valenti | |
| 7,000,951 B2 | 2/2006 | Valenti | |
| 7,017,293 B2 | 3/2006 | Riley | |
| 7,017,294 B2 | 3/2006 | Riley | |
| 7,047,682 B2 | 5/2006 | Riley | |
| 7,320,194 B2 | 1/2008 | Ali et al. | |
| 7,322,613 B2 | 1/2008 | Penuela et al. | |
| 7,454,854 B2 | 11/2008 | Riley | |
| 7,454,855 B2 | 11/2008 | Kotik et al. | |
| 7,461,473 B2 | 12/2008 | Riley | |
| 2004/0261644 A1 | 12/2004 | Stewart et al. | |
| 2005/0285385 A1 | 12/2005 | Bova et al. | |

(Continued)

FOREIGN PATENT DOCUMENTS

WO          WO 99/25565          5/1999

(Continued)

OTHER PUBLICATIONS

DataMate Laser Label/Wristband 9200, http://www.pdcorp.com/en-us/healthcare/9200-datamate-laser-label-wristbands.html.

(Continued)

*Primary Examiner*—Dana Ross
*Assistant Examiner*—Kyle Grabowski
(74) *Attorney, Agent, or Firm*—Ice Miller LLP

(57) ABSTRACT

A printable form comprising a printable face ply and a wristband releasably bonded to a surface of the printable face ply. In at least one embodiment the wristband may be detached from the surface of the printable face ply and secured to around a body part for use in identification. In at least one embodiment the printable face ply comprises one or more labels that may be detached therefrom and applied to the wristband.

1 Claim, 29 Drawing Sheets

U.S. PATENT DOCUMENTS

| | | |
|---|---|---|
| 2006/0113788 A1 | 6/2006 | Riley |
| 2006/0218837 A1 | 10/2006 | Riley |
| 2006/0236578 A1 | 10/2006 | Saint et al. |
| 2007/0120358 A1 | 5/2007 | Waggoner et al. |
| 2007/0283607 A1 | 12/2007 | Sloot |
| 2008/0067802 A1 | 3/2008 | Bell et al. |
| 2008/0098635 A1 | 5/2008 | Jain et al. |
| 2008/0109937 A1 | 5/2008 | Greer |
| 2008/0309065 A1 | 12/2008 | Ali et al. |

FOREIGN PATENT DOCUMENTS

| | | |
|---|---|---|
| WO | WO 2005/081928 | 9/2005 |

OTHER PUBLICATIONS

DataMate Mother/Father/Baby Laser Label Wristbands & ID Card 9204, http://www.pdcorp.com/en-us/ healthcare/9204-datamater-laser-label-wristbands.html.

Aug. 2005, Issue 3, Precision Dynamics Corporation Insider, Anderson Hospital Reduces Costs Improves Patent Safety with PDC Sentry Bar Code LabelBand Wristbands, www.pdcorp.com.

Laser Printed Identification Wristbands, http://relyco.com/laser_band.htm.

Original LaserBand Laser ID Wristbands, http://relyco.com/laserband_original.htm.

LaserBand 2 Laser ID Wristbands, http://relyco.com/laserband_2.htm.

FusionBand Self-Laminating Thermal Identification Wristbands, http://relyco.com/fusionband_thermal_wristband.htm.

Self-Laminating Laser Wristbands, Institute of Medicine. To Err is Human: Building a Safer Health System. Washington: National Academy Press: 1999: Bates DW. Spell N. Cullen DI. et al. The costs of adverse drug events in hospitalized patients. JAMA 1997:277.

Patient ID Expert.com, http://www.patientidexpert.com/laserwristbandstyle.html.

Omtool, http://www.omtool.com/products/healthcareMediaProducts.cfm.

Healthcare: A Solution for Positive Patient Identification, distributed by: Xerox Supplies Group, Rochester, New York 14644, Supplies Hotline 800 572-3273, web www.xerox.com/supplies.

Healthcare: A Solution for Positive Patient Identification, Self-Laminating Laser Wristbands, Russell F. Lewis, HIMSS Summer Conference 2002, Leape 1995 and California Healthcare Foundation 2001.

\* cited by examiner

LABEL SHEET WITH WRISTBAND

BACKGROUND

Identification wristbands are commonly used in a hospital or other setting to promote the easy identification of patients or other wearers. In the instance of a hospital use, a patient is generally provided with an identification wristband that is secured about the wrist of the patient upon admission to the hospital. In addition, a number of labels for use in identifying fluid samples, medications, charts, folders, papers and other common hospital objects specific to an admitted patient are often printed when a patient is admitted.

Often, the labels and wristbands are printed separately. The wristband is placed on the patient, while the labels are put into a patient chart, or otherwise saved for later use. However, in an effort to streamline patient admission procedures, and in light of the widespread use and low cost of computer driven printers such as laser printers, it has become desirable to print the labels and wristbands in a single step.

Accordingly, it is desired to provide an improved form of a combined wristband and printable label sheet.

SUMMARY

The present disclosure includes disclosure of a combined wristband and printable label sheet form. At least one embodiment of the present disclosure comprises a substrate material. At least one embodiment of the present disclosure comprises a substrate material comprising a face ply, where the face ply comprises a face ply surface; at least one release patch on the face ply surface; and a wristband with at least one adhesive stripe adhered to its underside surface. In at least one aspect of an embodiment of a printable form according to the present disclosure at least one adhesive stripe is releasably bonded to at least one release patch. In at least one aspect of an embodiment of a printable form according to the present disclosure, the wristband comprises a leading margin, a trailing margin, first and second side margins, a top side, and an underside, where the underside comprises an underside surface bounded by the leading margin, the trailing margin, and the first and second side margins, and where the leading margin, the trailing margin, and the first and second side margins are inboard of the leading edge, the trailing edge, and the first and second side edges of the substrate material. In at least one aspect of an embodiment of a printable form according to the present disclosure, a boundary of at least one label is defined in the face ply. In at least one aspect of an embodiment of a printable form according to the present disclosure, at least one label is removable from a liner ply and adherable to the wristband. In at least one aspect of an embodiment of a printable form according to the present disclosure, the wristband comprises a line of weakness, and at least one of the adhesive stripes is adhered to the underside surface on each side of the line of weakness. In at least one aspect of an embodiment of a printable form according to the present disclosure, the face ply comprises a material receptive to the application of indicia thereto. In at least one aspect of an embodiment of a printable form according to the present disclosure, the wristband comprises a material receptive to the application of indicia thereto. In at least one aspect of an embodiment of a printable form according to the present disclosure, the face ply comprises a second surface opposite the face ply surface, and the substrate material comprises a liner ply removably adhered to the second surface of the face ply.

At least one embodiment of the present disclosure comprises a method of making a printable form. Such a method according to at least one embodiment of the present disclosure may include the steps of providing a substrate material, where the substrate material comprises a liner ply and a face ply removably adhered to the liner ply; applying one or more release patches to a surface of the face ply, where the one or more release patches comprise a material capable of forming a releasable bond with an adhesive; providing a wristband material, where the wristband material has an undersurface; applying one or more stripes of adhesive to the undersurface; cutting one or more wristbands from the wristband material, where each of the wristbands comprises at least one stripe of adhesive; and applying at least one of the wristbands to the surface of the face ply such that at least one of the stripes of adhesive is in registration with and releasably bonded to at least one of the release patches. Such a method according to at least one embodiment of the present disclosure may include the step of defining a boundary of at least one label in the face ply. Such a method according to at least one embodiment of the present disclosure may include the step of cutting one or more discrete sheets from the substrate material, wherein each of the discrete sheets comprises at least one of the wristbands releasably bonded thereto. Such a method according to at least one embodiment of the present disclosure may include the step of folding the substrate material into two or more sheets, wherein each of the sheets comprises at least one of the wristbands releasably bonded thereto.

At least one embodiment of the present disclosure comprises a method of using a printable form. Such a method according to at least one embodiment of the present disclosure may include the steps of providing a printable form, where the printable form comprises a substrate material comprising a face ply, where the face ply comprises a face ply surface with at least one release patch on the face ply surface, and a wristband with at least one adhesive stripe adhered to its underside surface, where at least one of the adhesive stripes is releasably bonded to at least one release patch; removing the wristband by separating each adhesive stripe from its corresponding release patch, such that each adhesive stripe remains adhered to the underside surface; and securing the wristband around a body part. In at least one aspect of such a method according to at least one embodiment of the present disclosure, the step of securing the wristband around a body part comprises the step of adhering at least one of the adhesive stripes to the top side of the wristband. In at least one aspect of such a method according to at least one embodiment of the present disclosure, the step of securing the wristband around a body part comprises the step of adhering at least one of the adhesive stripes to another of the adhesive stripes. In at least one aspect of such a method according to at least one embodiment of the present disclosure where the substrate material comprises a liner ply removably adhered to the face ply and the face ply comprises a boundary of at least one label defined in the face ply, where each label is removably adhered to the liner ply, the method comprises the steps of removing at least one label from the face ply and apply the at least one removed label to the wristband.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION

Figure 1A:
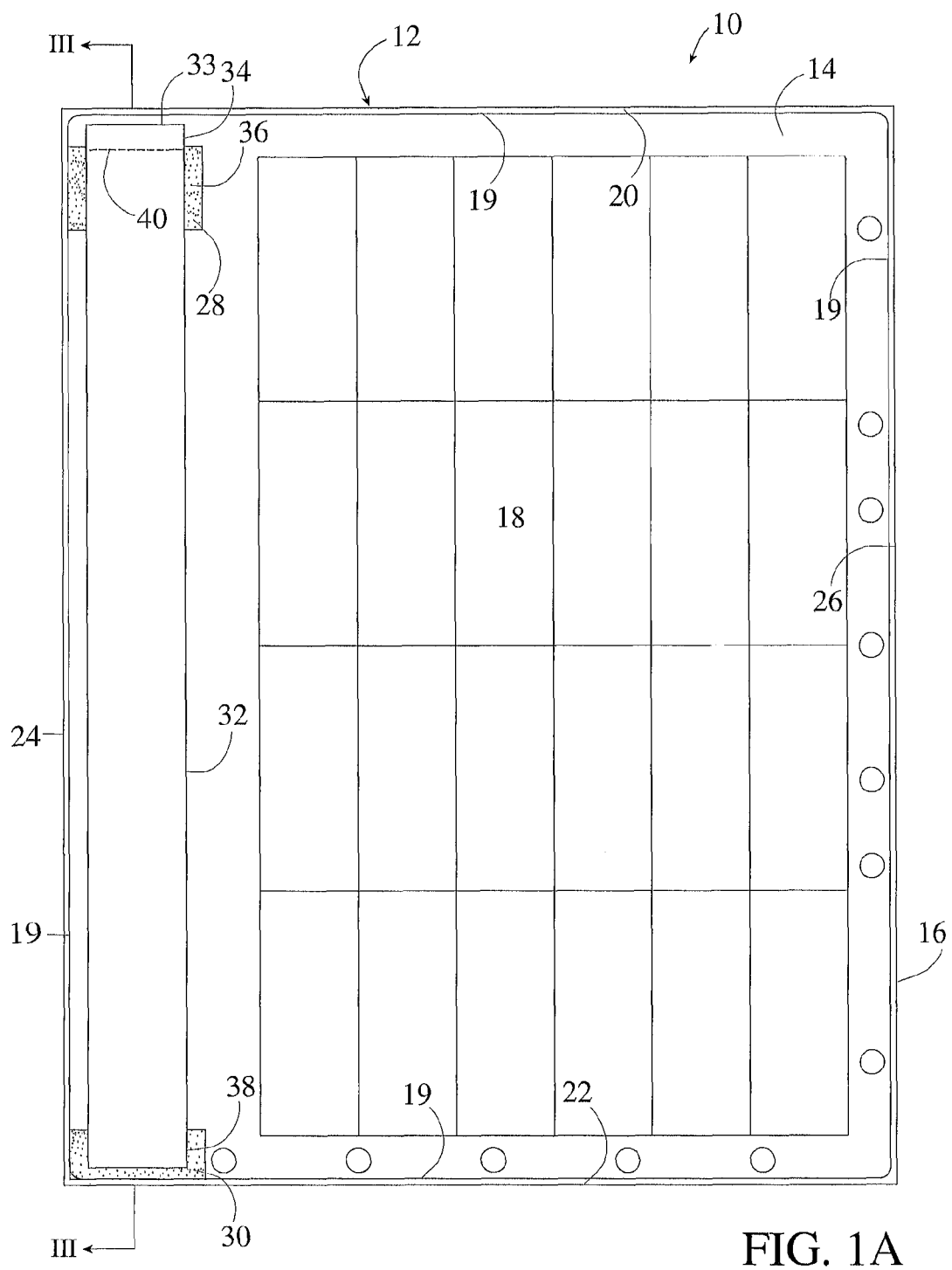
FIG. 1A shows a top view of a wristband label sheet according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1A shows a top view of wristband label sheet 10 according to at least one embodiment of the present disclosure. Shown in FIG. 1A are label sheet 12, comprising label material 14 and liner material 16. Adhesive 15 (not shown in FIG. 1A) is interposed between label material 14 and liner material 16 and removably adheres label material 14 to liner material 16. In at least one embodiment of the present disclosure, liner material 16 comprises a silicone coating on the surface facing adhesive 15. In the embodiment of wristband label sheet 10 shown in FIG. 1A, liner material 16 is bounded by leading edge 20, trailing edge 22, side edge 24, and side edge 26. Label sheet 12 may be of any size. In at least one embodiment of label sheet 12 according to the present disclosure, the outer dimensions of label sheet 12 are selected to enable label sheet 12 to fit in a commercially available printing device. For example, in such an embodiment, the outer dimensions of label sheet 12 may be 8½"×11", 8½"×14", or 210 mm×297 mm.

In at least one embodiment of the present disclosure, label material 14 comprises perimeter 19 defining a boundary of label material 14. In at least one embodiment of the present disclosure, at least a portion of perimeter 19 is inboard of the boundary formed by leading edge 20, trailing edge 22, side edge 24, and side edge 26. In at least one embodiment of the present disclosure, perimeter 19 is coextensive with the boundary formed by leading edge 20, trailing edge 22, side edge 24, and side edge 26.

In at least one embodiment of the present disclosure, label material 14 comprises a material suitable for the printing of indicia thereon, such as, for example, paper, polyester, or another polymer material. Indicia may be marked or printed on the top side of label material 14. For example, the top side of label material 14 may be exposed to an ink jet printer, a laser print, or another type of printing device capable of applying indicia to the top side of label material 14. The inks, toners, and/or other printing materials used in the application of indicia to the top side of label material 14 are selected to be compatible with the printing device used to apply such indicia, the material used for label material 14, and the intended use of wristband label sheet 10.

In the embodiment of wristband label sheet 10 shown in FIG. 1A, label material 14 comprises a plurality of labels 18. In at least one embodiment, labels 18 are die cut in label material 14. In at least one embodiment of the present disclosure, label material 14 comprises twenty-four labels 18, each having dimensions of about 1"×2.5". Other sizes and quantities of labels 18 are possible.

In the embodiment of wristband label sheet 10 shown in FIG. 1A, label material 14 comprises release patch 28 and release patch 30. Release patches 28, 30 comprise areas of a release coating (such as, for example, a silicone) applied to the surface of label material 14, to allow the removable adherence of wristband 32 to label sheet 14, as discussed hereinafter. In at least one embodiment of the present disclosure, release patches 28, 30 comprise free radical ultraviolet cured silicone. In at least one embodiment of the present disclosure, release patches 28, 30 comprise a cationic ultraviolet cured release coating. Alternatively, any type of coating (including no-silicone coatings) that permits the removable adherence of wristband 32 to label sheet 14 may be used.

Also shown in the embodiment of wristband label sheet 10 shown in FIG. 1A is wristband 32 comprising stub 33 and line of weakness 40. In at least one embodiment of the present disclosure, line of weakness 40 comprises a series of perforations. In at least one embodiment of the present disclosure, wristband 32 (including stub 33) is constructed of a polyester material, although other materials suitable for the intended use of wristband 32 may be used. In at least one embodiment of the present disclosure, wristband 32 has dimensions of about 1"×10.75", however wristband 32 may be of any size that fits on label sheet 12.

Figure 1B:
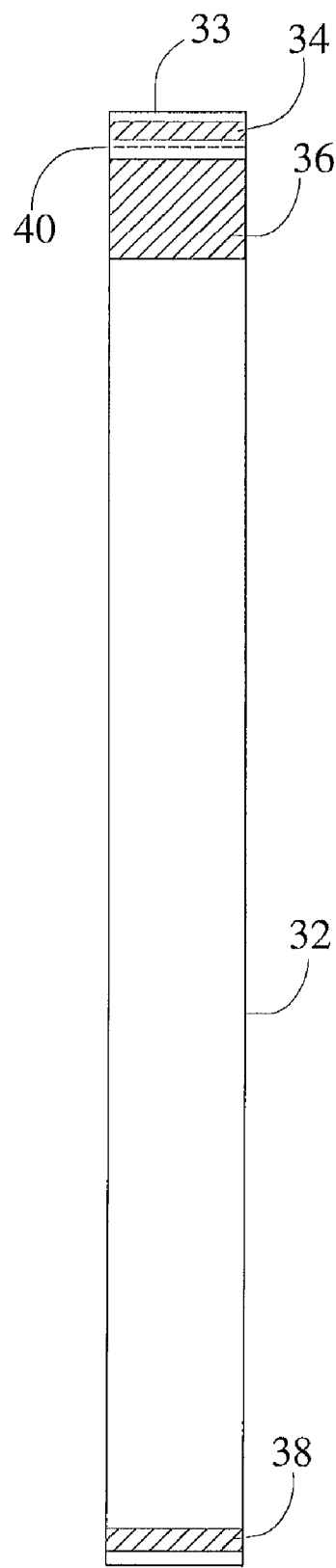
FIG. 1B shows the underside of a wristband according to at least one embodiment of the present disclosure.

FIG. 1B shows the underside of wristband 32 before attachment to label sheet 12, according to at least one embodiment of the present disclosure. Shown in FIG. 1B are wristband 32 comprising stub 33, adhesive stripe 34, adhesive stripe 36, adhesive stripe 38, and line of weakness 40. In at least one embodiment of the present disclosure, adhesive stripes 34, 36, 38 comprise a layer of a hot melt adhesive.

Referring back to FIG. 1A, shown therein are the locations of adhesive stripes 34, 36, 38 on the underside of wristband 32. Adhesive stripe 34 is interposed between label material 14 and stub 33, and adheres label material 14 to stub 33. In at least one embodiment of the present disclosure, adhesive stripe 34 is oriented toward leading edge 20 of label sheet 12. Adhesive stripe 36 is interposed between wristband 32 and release patch 28 and removably adheres wristband 32 to release patch 28. Adhesive stripe 38 is interposed between wristband 32 and release patch 30 and removably adheres wristband 32 to release patch 30. As discussed hereinafter, adhesive stripes 36, 38 are operable to secure wristband 32 around a subject's wrist after wristband 32 is removed from label sheet 12.

In at least one alternative embodiment of the present disclosure, release patch 28 and adhesive stripe 36 may be omitted from wristband label sheet 10. In such an embodiment adhesive stripe 34 remains and is interposed between label material 14 and stub 33 to adhere label material 14 to stub 33. In such an embodiment adhesive stripe 38 remains and is interposed between wristband 32 and release patch 30 to removably adhere wristband 32 to release patch 30.

In at least one alternative embodiment of the present disclosure, adhesive stripes 36, 38 comprise a repositionable adhesive. In such an embodiment release patches 28, 30 may be omitted from wristband label sheet 10. In at least one other alternative embodiment of the present disclosure, a wristband label sheet comprises a stub at each end of the wristband.

Indicia may be marked or printed on the top side of wristband 32. For example, the top side of wristband 32 may be exposed to an ink jet printer, a laser print, or another type of printing device capable of applying indicia to the top side of wristband 32. Indicia may be printed on wristband 32 before, after, or concurrently with the printing of indicia on label material 14. The inks, toners, and/or other printing materials used in the application of indicia to the top side of wristband 32 are selected to be compatible with the printing device used to apply such indicia, the material used for wristband 32, and the intended use of wristband 32.

Figure 1C:
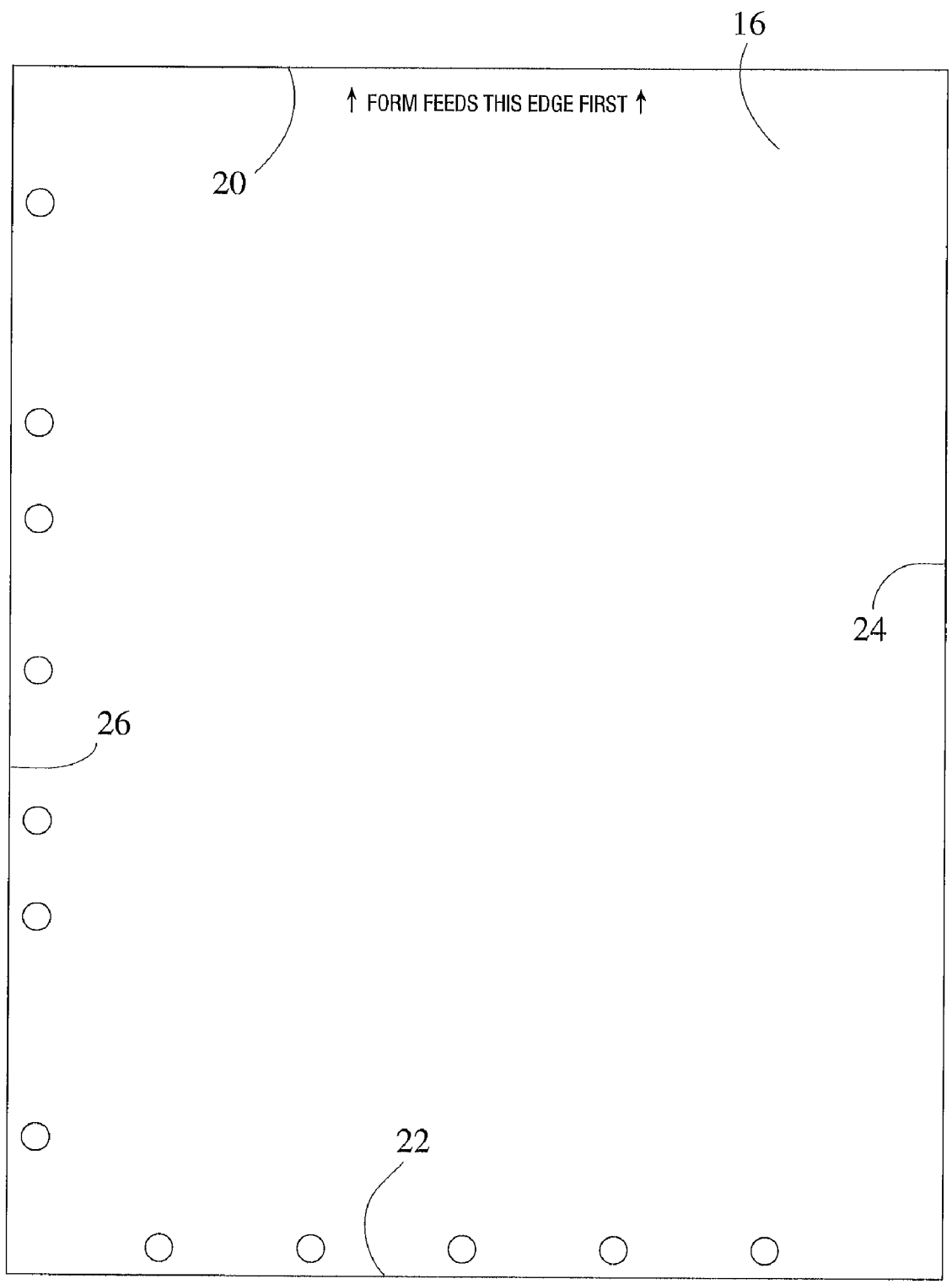
FIG. 1C shows a bottom view of wristband label sheet according to at least one embodiment of the present disclosure.

FIG. 1C shows a bottom view of wristband label sheet 10 of FIG. 1A. Shown in FIG. 1C is liner 16, bounded by leading edge 20, trailing edge 22, side edge 24, and side edge 26.

Figure 2A:
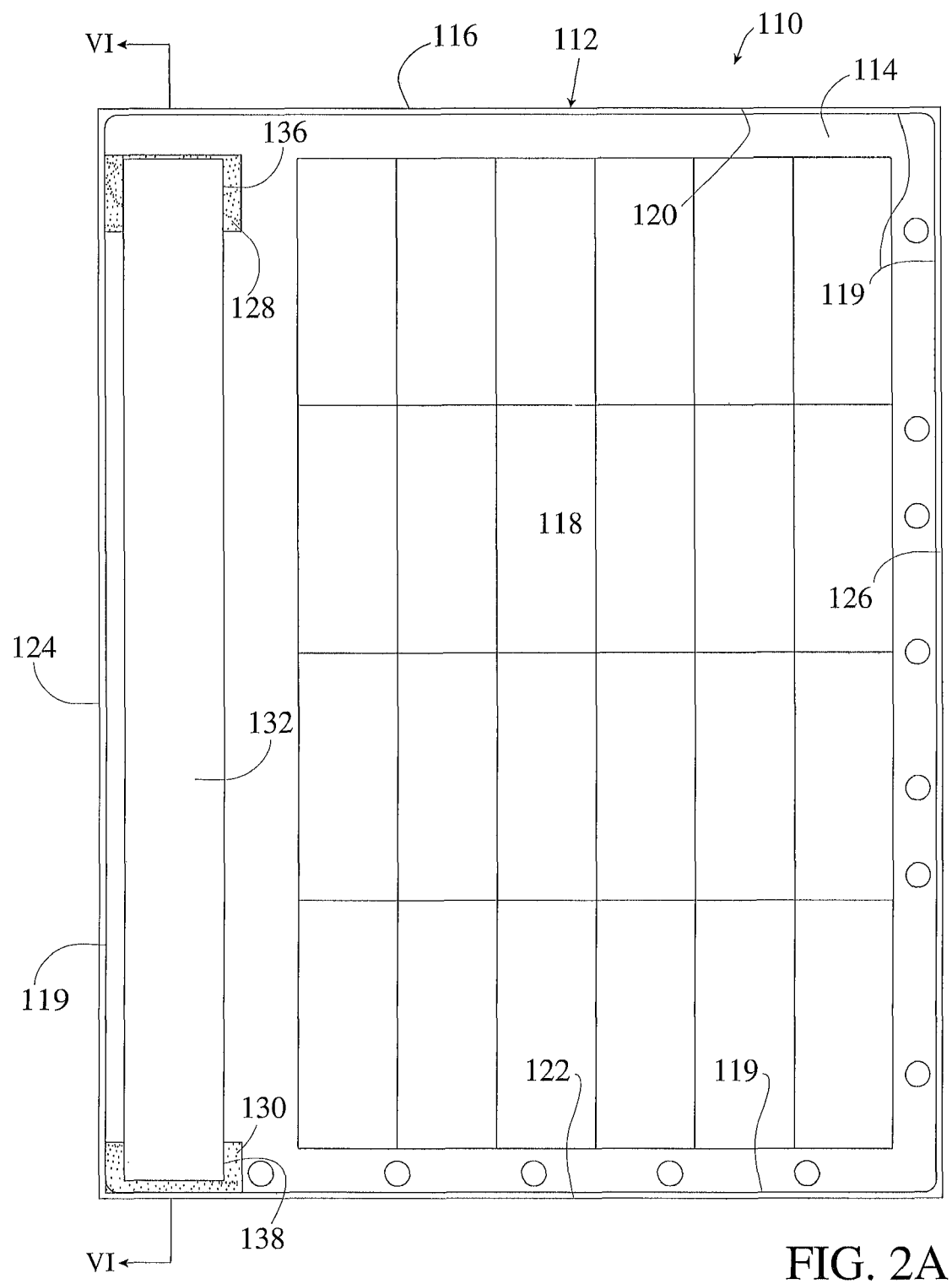
FIG. 2A shows a top view of a wristband label sheet according to at least one embodiment of the present disclosure.

FIG. 2A shows a top view of wristband label sheet 110 according to at least one embodiment of the present disclosure. Shown in FIG. 2A are label sheet 112, comprising label material 114 and liner material 116. Adhesive 115 (not shown in FIG. 2A) is interposed between label material 114 and liner material 116 and removably adheres label material 114 to liner material 116. In at least one embodiment of the present disclosure, liner material 116 comprises a silicone coating on the surface facing adhesive 115. In the embodiment of wristband label sheet 110 shown in FIG. 2A, liner material 116 is bounded by leading edge 120, trailing edge 122, side edge 124, and side edge 126. Label sheet 112 may be of any size. In at least one embodiment of label sheet 112 according to the present disclosure, the outer dimensions of label sheet 112 are selected to enable label sheet 112 to fit in a commercially available printing device. For example, in such an embodiment, the outer dimensions of label sheet 112 may be 8½"×11", 8½"×14", or 210 mm×297 mm.

In at least one embodiment of the present disclosure, label material 114 comprises perimeter 119 defining a boundary of label material 114. In at least one embodiment of the present disclosure, at least a portion of perimeter 119 is inboard of the boundary formed by leading edge 120, trailing edge 122, side edge 124, and side edge 126. In at least one embodiment of the present disclosure, perimeter 119 is coextensive with the boundary formed by leading edge 120, trailing edge 122, side edge 124, and side edge 126.

In at least one embodiment of the present disclosure, label material 114 comprises a material suitable for the printing of indicia thereon, such as, for example, paper, polyester, or another polymer material. Indicia may be marked or printed on the top side of label material 114. For example, the top side of label material 114 may be exposed to an ink jet printer, a laser print, or another type of printing device capable of applying indicia to the top side of label material 114. The inks, toners, and/or other printing materials used in the application of indicia to the top side of label material 114 are selected to be compatible with the printing device used to apply such indicia, the material used for label material 114, and the intended use of wristband label sheet 110.

In the embodiment of wristband label sheet 110 shown in FIG. 2A, label material 114 comprises a plurality of labels 118. In at least one embodiment, labels 118 are die cut in label material 114. In at least one embodiment of the present disclosure, label material 114 comprises twenty-four labels 118, each having dimensions of about 1"×2.5". Other sizes and quantities of labels 118 are possible.

In the embodiment of wristband label sheet 110 shown in FIG. 2A, label material 114 comprises release patch 128 and release patch 130. Release patches 128, 130 comprise areas of a release coating (such as, for example, a silicone) applied to the surface of label material 114, to allow the removable adherence of wristband 132 to label sheet 114, as discussed hereinafter. In at least one embodiment of the present disclosure, release patches 128, 130 comprise free radical ultraviolet cured silicone. In at least one embodiment of the present disclosure, release patches 128, 130 comprise a cationic ultraviolet cured release coating. Alternatively, any type of coating (including no-silicone coatings) that permits the removable adherence of wristband 132 to label sheet 114 may be used.

Also shown in the embodiment of wristband label sheet 110 shown in FIG. 2A is wristband 132. In at least one embodiment of the present disclosure, wristband 132 is constructed of a polyester material, although other materials suitable for the intended use of wristband 132 may be used. In at least one embodiment of the present disclosure, wristband 132 has dimensions of about 1"×10.75", however wristband 132 may be of any size that fits on label sheet 112.

Figure 2B:
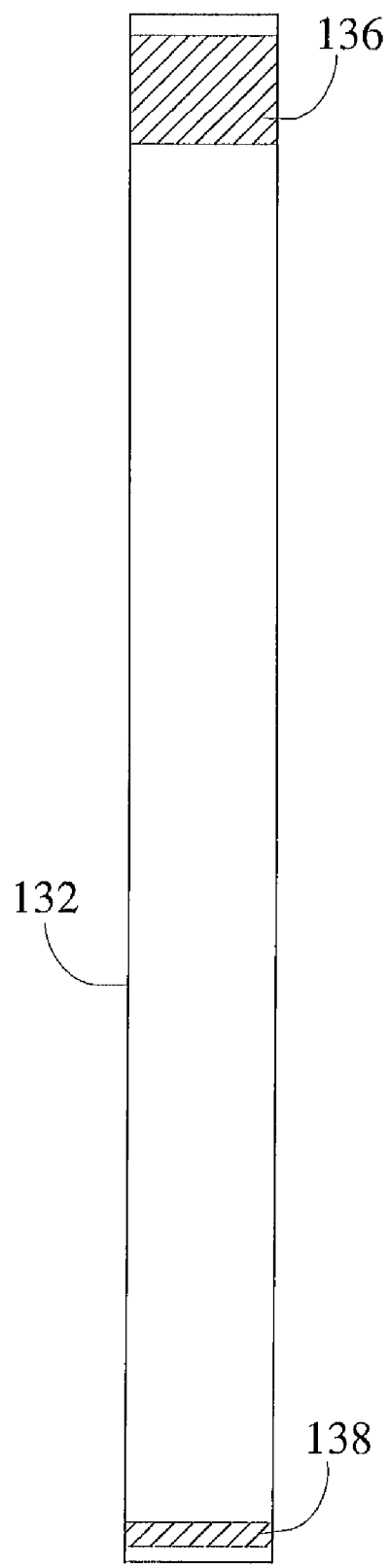
FIG. 2B shows the underside of a wristband according to at least one embodiment of the present disclosure.

FIG. 2B shows the underside of wristband 132 before attachment to label sheet 112, according to at least one embodiment of the present disclosure. Shown in FIG. 2B are wristband 132 comprising adhesive stripe 136 and adhesive stripe 138. In at least one embodiment of the present disclosure, adhesive stripes 136, 138 comprise a layer of a hot melt adhesive.

Referring back to FIG. 2A, shown therein are the locations of adhesive stripes 136, 138 on the underside of wristband 132. Adhesive stripe 136 is interposed between wristband 132 and release patch 128 and removably adheres wristband 132 to release patch 128. Adhesive stripe 138 is interposed between wristband 132 and release patch 130 and removably adheres wristband 132 to release patch 130. As discussed hereinafter, adhesive stripes 136, 138 are operable to secure wristband 132 around a subject's wrist after wristband 132 is removed from label sheet 112.

In at least one alternative embodiment of the present disclosure, adhesive stripes 136, 138 comprise a repositionable adhesive. In such an embodiment release patches 128, 130 may be omitted from wristband label sheet 110.

Indicia may be marked or printed on the top side of wristband 132. For example, the top side of wristband 132 may be exposed to an ink jet printer, a laser print, or another type of printing device capable of applying indicia to the top side of wristband 132. Indicia may be printed on wristband 132 before, after, or concurrently with the printing of indicia on label material 114. The inks, toners, and/or other printing materials used in the application of indicia to the top side of wristband 132 are selected to be compatible with the printing device used to apply such indicia, the material used for wristband 132, and the intended use of wristband 132.

Figure 2C:
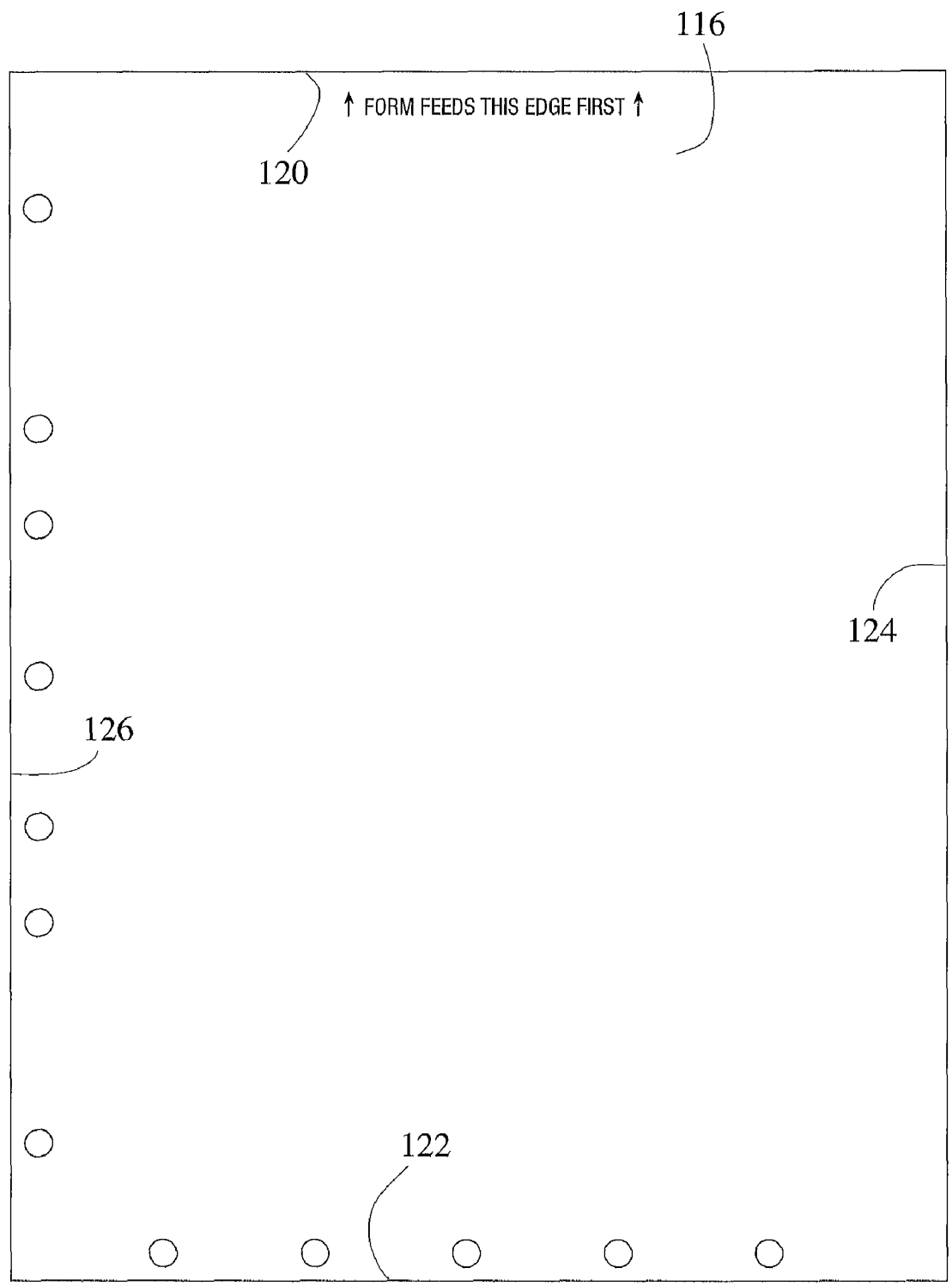
FIG. 2C shows a bottom view of wristband label sheet according to at least one embodiment of the present disclosure.

FIG. 2C shows a bottom view of wristband label sheet 110 of FIG. 2A. Shown in FIG. 2C is liner 116, bounded by leading edge 120, trailing edge 122, side edge 124, and side edge 126.

Figure 3:
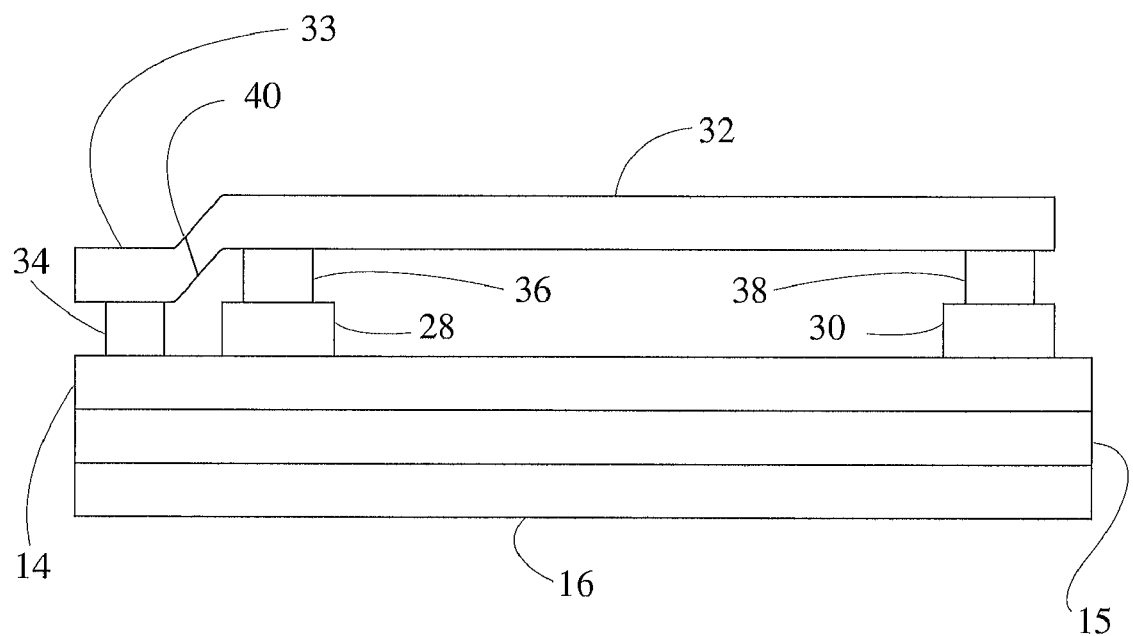
FIG. 3 shows a cross-sectional view of an embodiment of a wristband label sheet according to at least one embodiment of the present disclosure.

FIG. 3 shows a cross-sectional view of the embodiment of wristband label sheet 10 of FIG. 1A taken on line of III-III FIG. 1A, with the proportions enhanced for purposes of clarity. Shown in FIG. 3 are label material 14, adhesive layer 15, liner material 16, release patch 28, release patch 30, wristband 32, stub 33, adhesive stripe 34, adhesive stripe 36, adhesive stripe 38, and line of weakness 40.

Figure 4:
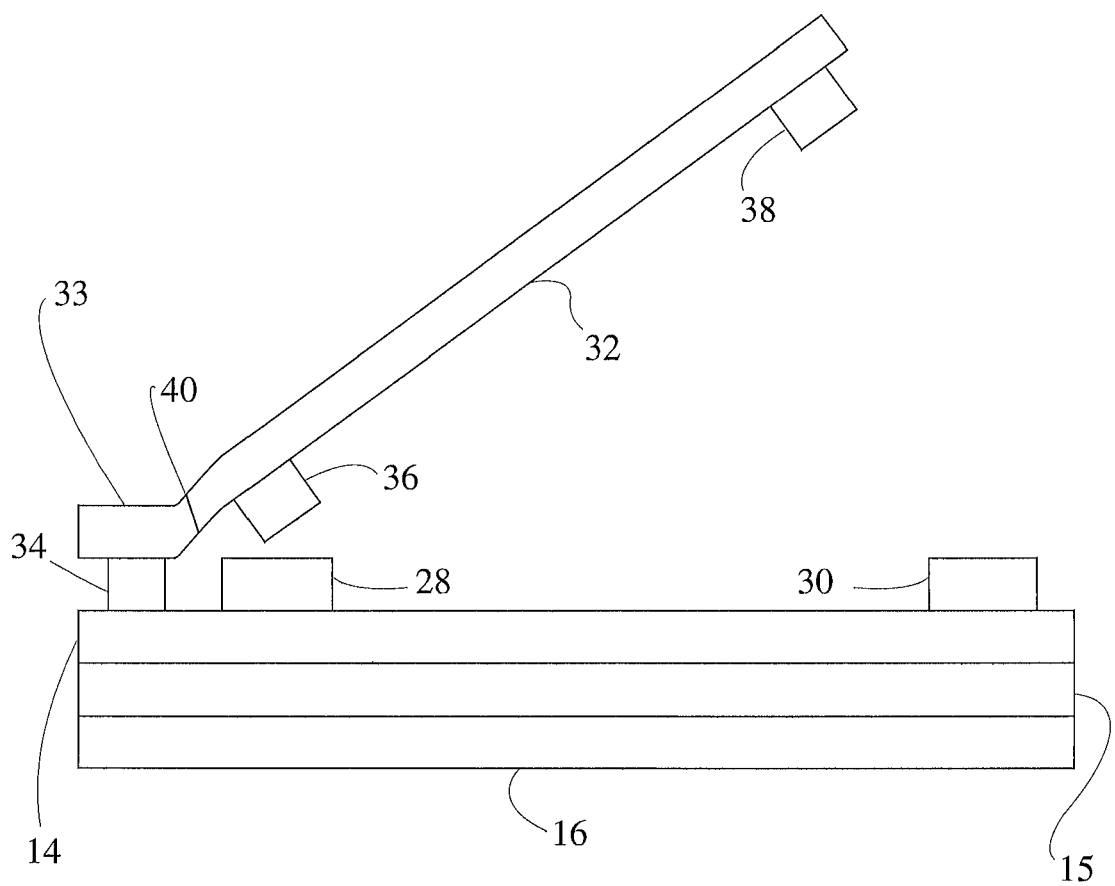
FIG. 4 shows a cross-sectional view of an embodiment of a wristband label sheet according to at least one embodiment of the present disclosure.

According to at least one embodiment of the present disclosure, wristband 32 is removable from label sheet 12 by grasping wristband 32 between adhesive stripe 36 and adhesive stripe 38 and pulling wristband 32 away from label sheet 12. FIG. 4 shows a cross-sectional view of an embodiment of wristband label sheet 10 according to at least one embodiment of the present disclosure, with the proportions enhanced for purposes of clarity. As shown in FIG. 4, wristband 32 is partially separated from label sheet 12. As shown in FIG. 4, adhesive stripe 36 and adhesive stripe 38 have separated from release patch 28 and release patch 30, respectively. Release patch 28 and release patch 30 remain on the top surface of label material 14. Adhesive stripe 36 and adhesive stripe 38 remain adhered to the underside of wristband 32. Stub 33 remains adhered to the top surface of label material 14 by adhesive stripe 34. Wristband 32 remains attach to stub 33 at line of weakness 40.

Figure 5:
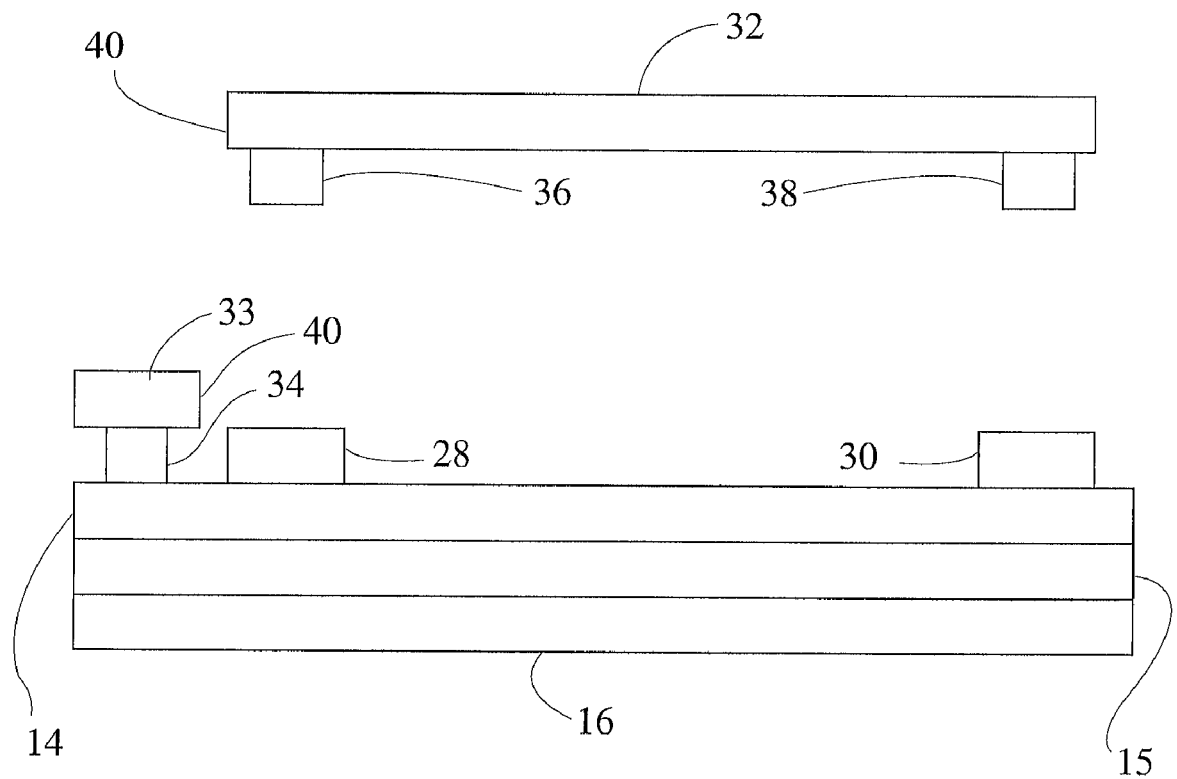
FIG. 5 shows a cross-sectional view of an embodiment of a wristband label sheet according to at least one embodiment of the present disclosure.

FIG. 5 shows a cross-sectional view of an embodiment of wristband label sheet 10 according to at least one embodiment of the present disclosure, with the proportions enhanced for purposes of clarity. As shown in FIG. 5, wristband 32 is fully separated from label sheet 12, and wristband 32 is separated from stub 33 at line of weakness 40. Stub 33 remains adhered to the top surface of label material 14 by adhesive stripe 34. As shown in FIG. 5, adhesive stripes 36, 38 remain adhered to the underside of wristband 32, and release patch 28 and release patch 30 remain adhered to label material 14.

Figure 6:
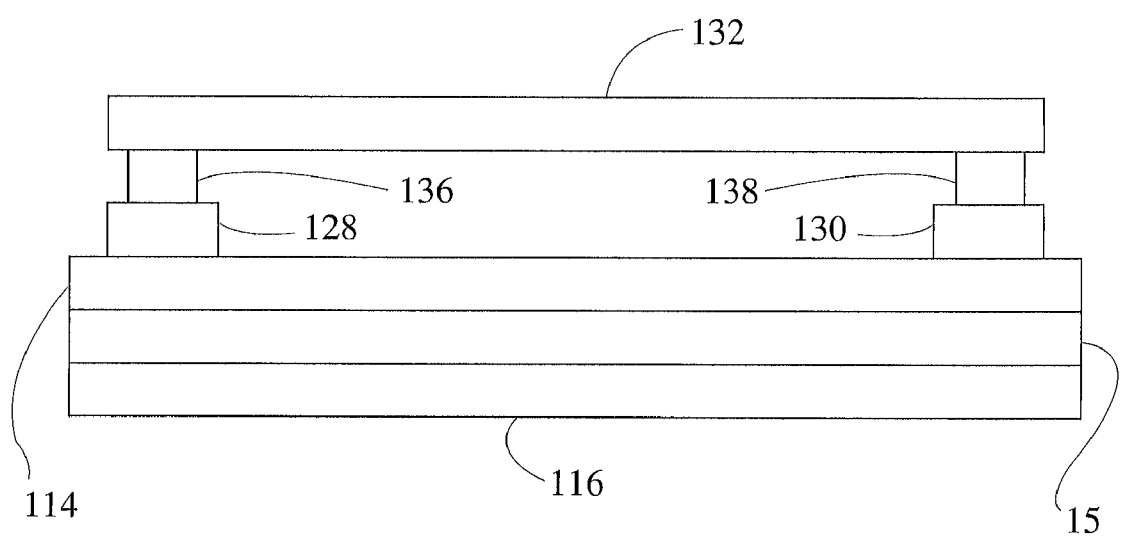
FIG. 6 shows a cross-sectional view of an embodiment of a wristband label sheet according to at least one embodiment of the present disclosure.

FIG. 6 shows a cross-sectional view of the embodiment of wristband label sheet 110 of FIG. 2A taken on line VI-VI of FIG. 2A, with the proportions enhanced for purposes of clarity. Shown in FIG. 6 are label material 114, adhesive layer 115, liner material 116, release patch 128, release patch 130, wristband 132, adhesive stripe 136, and adhesive stripe 138.

Figure 7:
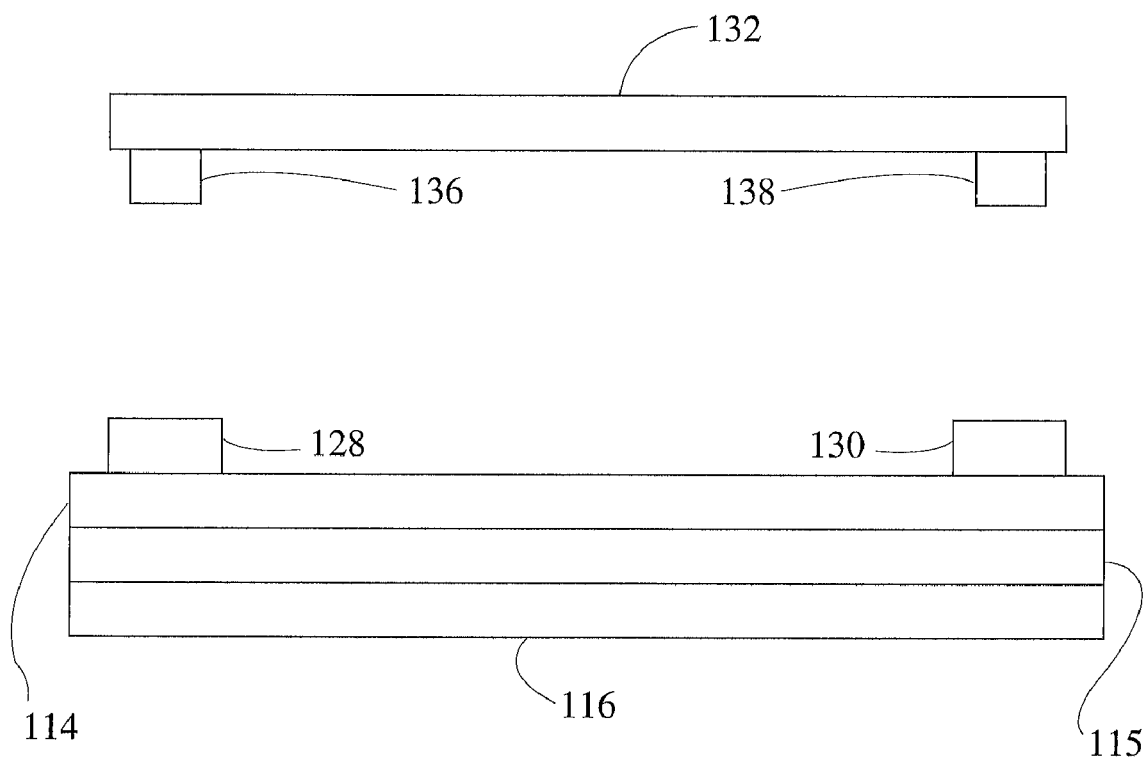
FIG. 7 shows a cross-sectional of an embodiment of a wristband label sheet according to at least one embodiment of the present disclosure.

According to at least one embodiment of the present disclosure, wristband 132 is removable from label sheet 112 by grasping wristband 132 between adhesive stripe 136 and adhesive stripe 138 and pulling wristband 132 away from label sheet 112. FIG. 7 shows a cross-sectional view of an embodiment of wristband label sheet 110 according to at least one embodiment of the present disclosure, with the proportions enhanced for purposes of clarity. As shown in FIG. 7, wristband 132 is separated from label sheet 112. As shown in FIG. 7, adhesive stripe 136 and adhesive stripe 138 have separated from release patch 128 and release patch 130, respectively. Release patch 128 and release patch 130 remain on the top surface of label material 114. Adhesive stripe 136 and adhesive stripe 138 remain adhered to the underside of wristband 132.

Figure 8A:
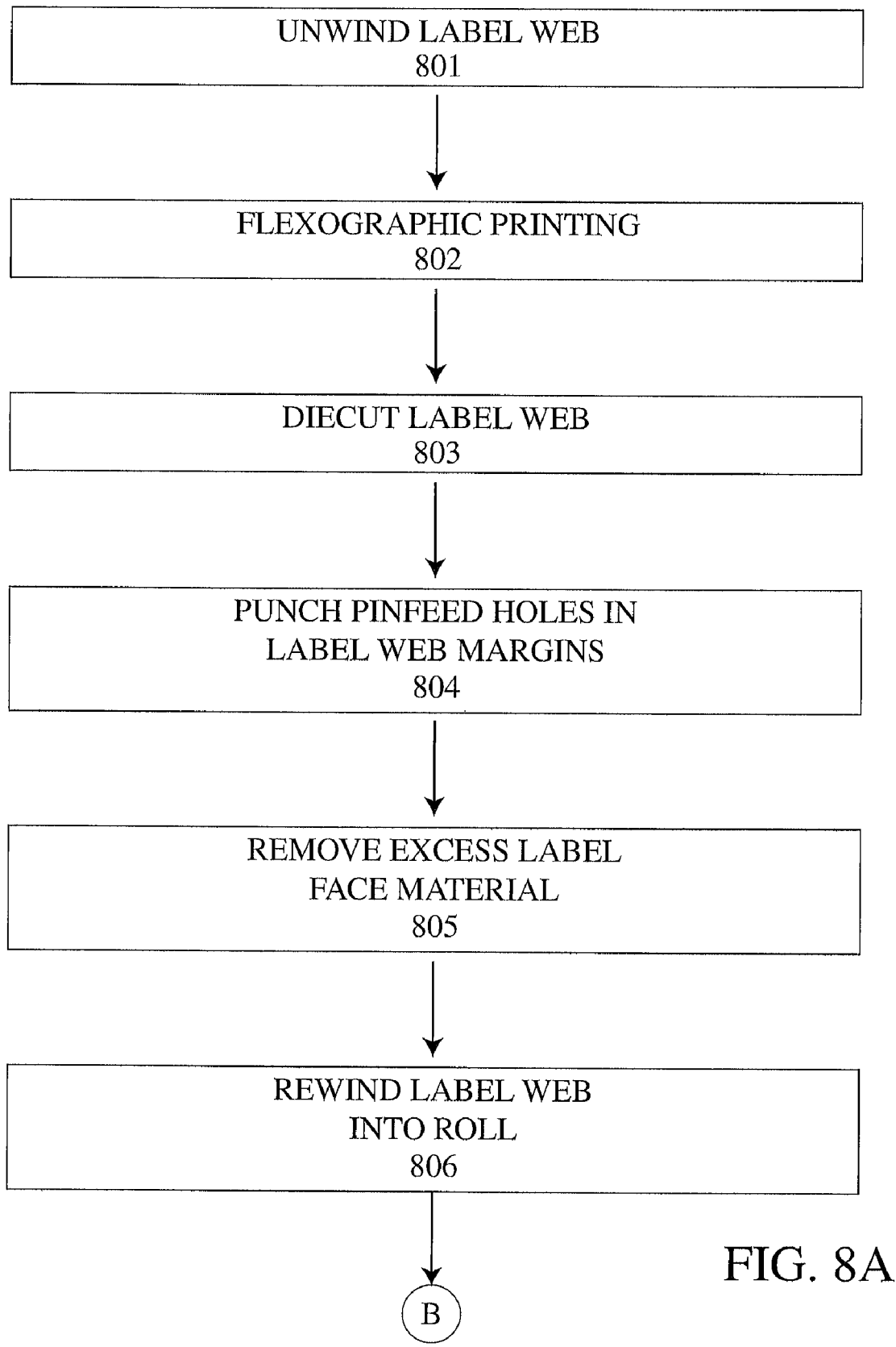
FIGS. 8A-C shows a flowchart for a process for manufacturing a wristband label sheet according to at least one embodiment of the present disclosure.
Figure 8B:
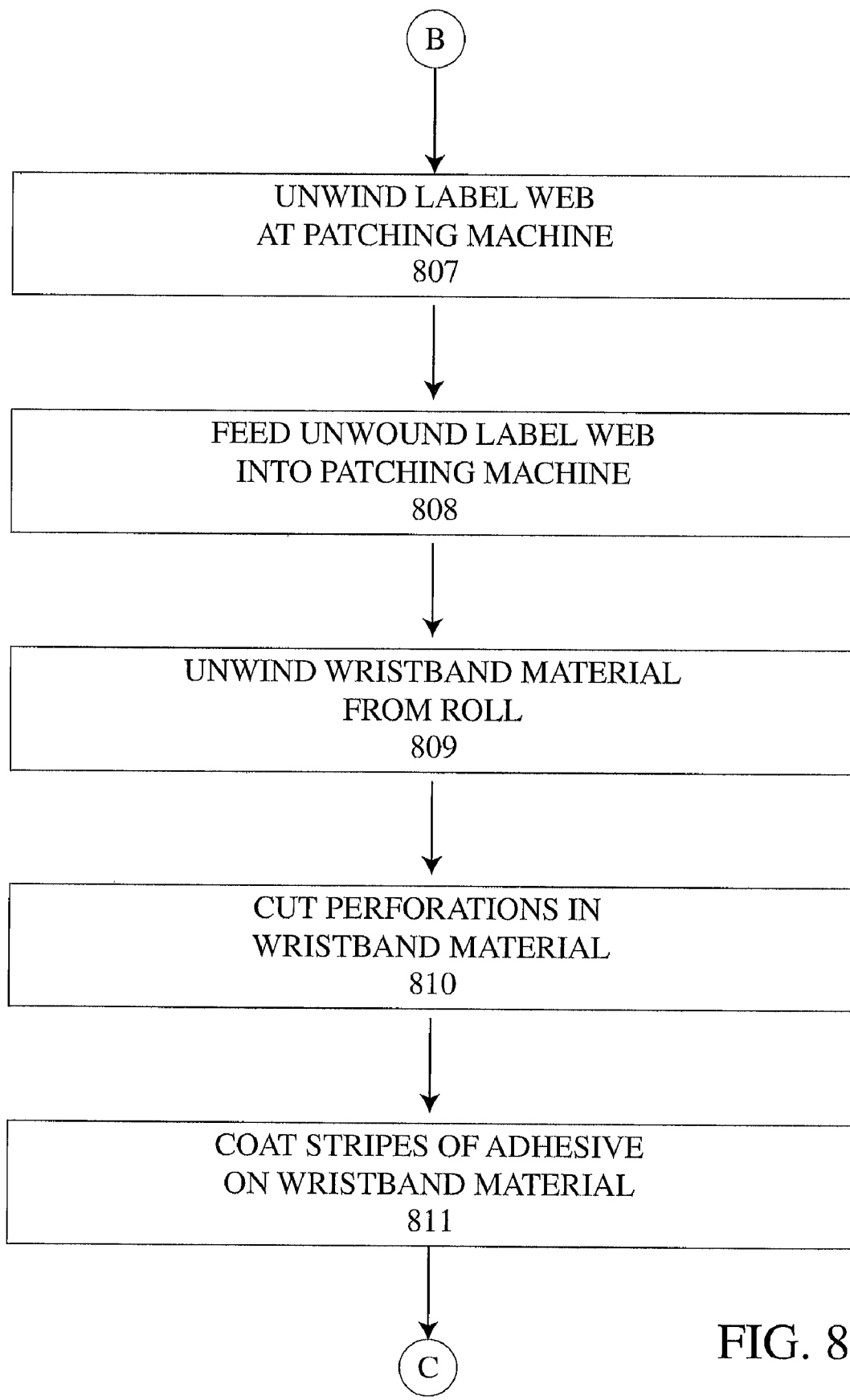
Figure 8C:
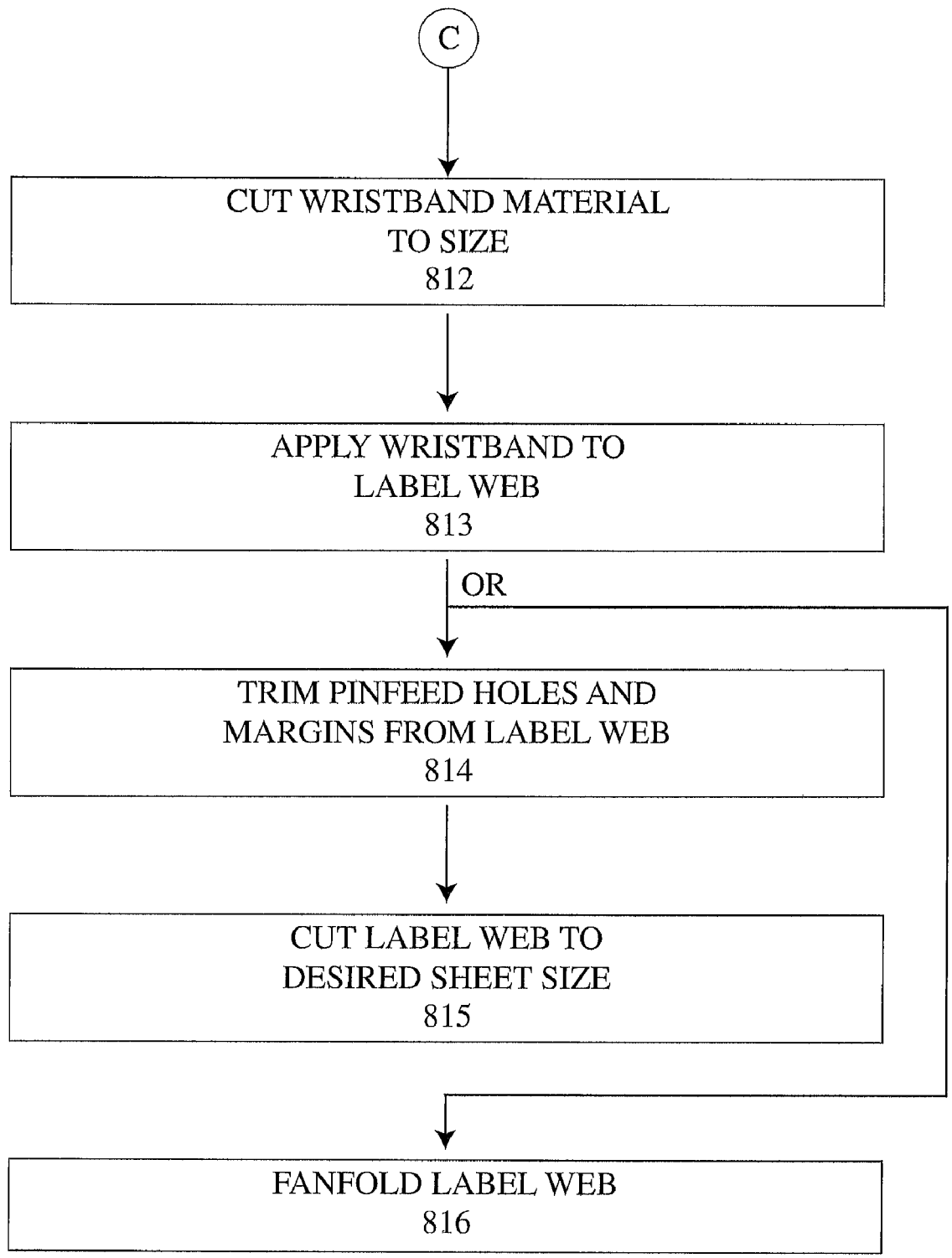

FIGS. 8A-C shows a flowchart illustrating a process for manufacturing a wristband label sheet according to at least one embodiment of the present disclosure.

In step 801 of the embodiment of the present disclosure shown in FIG. 8A, a web of label material comprising a silicone coated liner, label face material, and a pressure sensitive adhesive interposed between the silicone coated liner and label face material, is unwound from a roll and fed mechanically into one or more flexographic printing presses. According to at least on embodiment of the present disclosure, the web of label material comprises an edge margin of at least about ½" on each edge, such that the overall width of web of label material is 1" greater than the desired width of the finished product.

Alternatively, separate webs of liner material and label face material may be unwound from a roll and fed mechanically into a process by which a pressure sensitive adhesive is applied to either the liner material or label face material, and then the liner material and label face material are laminated to together with the pressure sensitive adhesive interposed between the liner material and label face material. In such an application the pressure sensitive adhesive may be coated edge to edge or it may be coated in a pattern with voids of adhesive where required.

In step 802 of the embodiment of the present disclosure shown in FIG. 8A, one or more flexographic printing presses apply one or more release patches comprising silicone or another type of release coating to the surface of the label face material. Such flexographic printing presses also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 8A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 803 of the embodiment of the present disclosure shown in FIG. 8A, after the flexographic printing step, the web of label material then travels through rotary die stations, where the web of label material can be die cut to create multiple labels, label cavities, slits, peel tabs, lines of weakness, perforations, punched holes for insertion into binders or folders, or any other specified die cutting. Such die cutting may be die cutting of the label face material only, the liner material only, or both the label face material and the liner material.

In step 804 of the embodiment of the present disclosure shown in FIG. 8A, the web of label material proceeds to a punching station where pinfeed holes are punched in ½" margins at each edge of the web of label material, to facilitate registration of the web of label material in the process during which wristbands are applied to the web of label material (discussed hereinafter).

In step 805 of the embodiment of the present disclosure shown in FIG. 8A, if required for the wristband label sheet design, portions of the label face material are removed. For example, it may be required for the wristband label sheet design that the border comprising the outer edges of the label face material be removed prior to delivery to a customer. In such a case, the border can be separated from the portion of the label face material that is desired to remain by a die cut through the label face material only, and then the waste at the border of the label face material can be peeled off at a waste removal station and then wound on a waste roll or sucked away by a vacuum removal system.

In step 806 of the embodiment of the present disclosure shown in FIG. 8A, after printing of release patches, die cutting, and punching of pinfeed holes, the web of label material is rewound onto rolls that will be furnished to the patching machine process.

In step 807 of the embodiment of the present disclosure shown in FIG. 8B, the rolled web of label material from step 807 is unwound and fed into a patching machine, wherein one or more wristbands will be applied to the web of label material.

In at least one alternative embodiment of the present disclosure, the steps shown as step 806 and step 807 of the embodiment of the present disclosure shown in FIG. 8B may be omitted. In such an embodiment, the web of label material proceeds to step 808 of the embodiment of the present disclosure shown in FIG. 8B.

In step 808 of the embodiment of the present disclosure shown in FIG. 8B, the punched pinfeed holes in the web of label material engage with a pinfeed mechanism of the patching machine. The pinfeed mechanism of the patching machine pulls the web of label material into and through the patching machine by pins that penetrate the previously punched pinfeed holes and rotate on gear driven shafts to drive the web of label material through the patching machine at a predetermined feed rate.

In step 809 of the embodiment of the present disclosure shown in FIG. 8B, a roll of wristband material (such as, for example, a roll of a polyester material) is unwound mechanically and fed into the patching machine. According to at least on embodiment of the present disclosure, the width of the wristband material on the roll of wristband material is the same as the desired width of the wristband to be applied to applied to the web of label material (discussed hereinafter).

In step 810 of the embodiment of the present disclosure shown in FIG. 8B, if required for the wristband label sheet design, lines of weakness are cut into the unrolled wristband material at a perforating station.

In step 811 of the embodiment of the present disclosure shown in FIG. 8B, the patching machine coats one or more stripes of adhesive on the underside the web of wristband material polyester at an adhesive coating station.

In step 812 of the embodiment of the present disclosure shown in FIG. 8C, the patching machine cuts each wristband to a predetermined length. For example, if the finished product required a 1" long wristband, the patching machine cuts off a 1" length of wristband material from the roll of wristband material. In an exemplary embodiment where a 1" long, 10.75" wide wristband is to be applied to an 8.5" long label sheet, the 10.75" wide web of wristband material is fed by computer controlled nip type feed rollers at a rate of 1" for every 8.5" of label material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder.

In step 813 of the embodiment of the present disclosure shown in FIG. 8C, after the wristband is cut to length, the vacuum cylinder carries each cut-off wristband to an impression roller that is wrapped by the web of label material. At the impression roller the wristband is transferred from the vacuum cylinder to the face of the web of label material. The wristband is applied such that one or more of the adhesive stripes on the underside of the wristband are aligned with one or more of the release patches on the label face material. The wristband is adhered to the web of label material by the adhesive stripes that were applied to the underside of the wristband. The patching machine comprises gearing that keeps the cutting cylinder and vacuum cylinder in time with the pace at which the patching machine's pinfeed mechanism moves the web of label material.

In step 814 of the embodiment of the present disclosure shown in FIG. 8C, if required for the wristband label sheet design, the ½" margins (including the pinfeed holes) are mechanically trimmed off of the web of label material at a trimming station.

In step 815 of the embodiment of the present disclosure shown in FIG. 8C, if required for the wristband label sheet design, the web of label material including the applied wristband is mechanically cut into sheets at a sheeter station, with each sheet containing one or more wristbands as required by the wristband label sheet design. The sheets are fed into a batcher/stacker, and then may be shrink-wrapped and packaged. Sheeting is an alternative to the fanfolding step discussed hereinafter.

In step 816 of the embodiment of the present disclosure shown in FIG. 8C, if required for the wristband label sheet design, the web of label material including the applied wristband may be fanfolded in-line with a mechanical folder or by gravity in waterfall fashion, with each fanfold containing one or more wristbands as required by the wristband label sheet design. The wristband label sheet design may require the ½" margins with pinfeed holes to be left on the fanfolded web of label material. Fanfolding is an alternative to the sheeting step discussed above.

Figure 9:
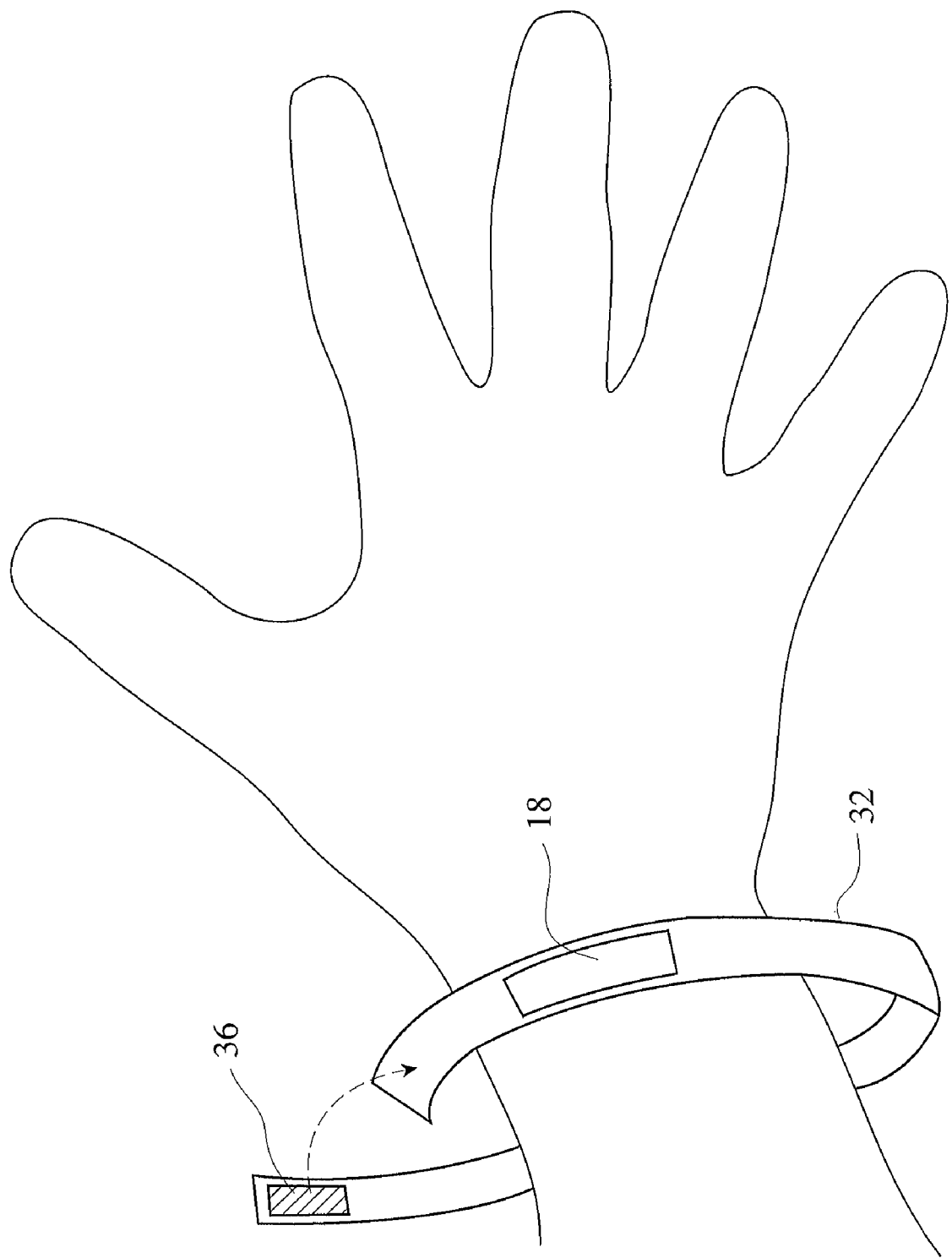
FIG. 9 shows an illustration of at least one embodiment of a wristband according to the present disclosure in use.

FIG. 9 shows at least one embodiment of a wristband according to the present disclosure in use. As shown in FIG. 9, wristband 32 is looped around the wrist of a subject, and the ends of wristband 32 are adhered together using one or more of adhesive stripes 36, 38. Optionally, one or more labels 18 may be removed from liner material 16 and adhered to wristband 32. Such labels 18 may comprise printed indicia.

Figure 10A:
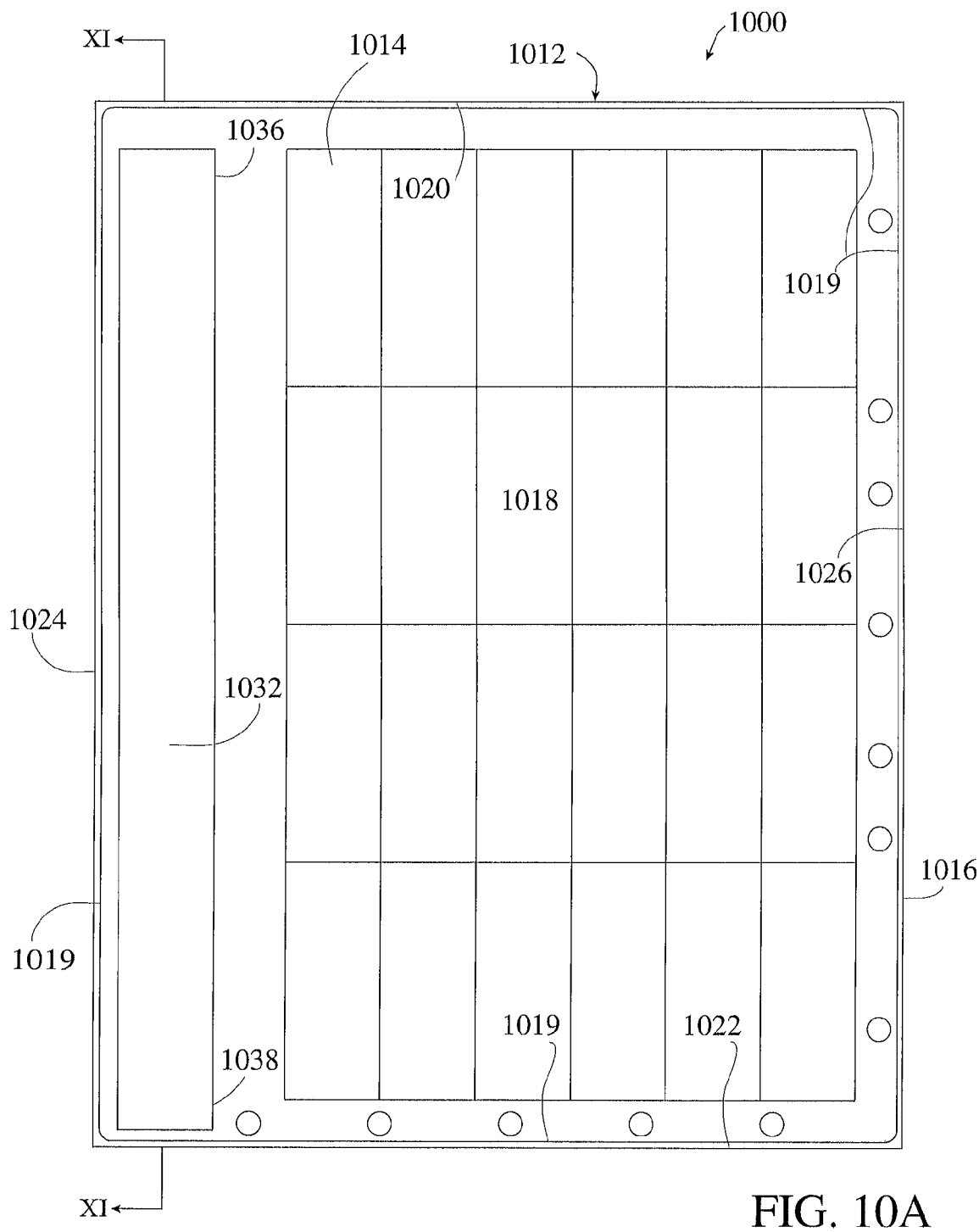
FIG. 10A shows a top view of a wristband label sheet according to at least one embodiment of the present disclosure.

FIG. 10A shows a top view of wristband label sheet 1000 according to at least one embodiment of the present disclosure. Shown in FIG. 10A are label sheet 1012, comprising label material 1014 and liner material 1016. Adhesive 1015 (not shown in FIG. 10A) is interposed between label material 1014 and liner material 1016 and removably adheres label material 1014 to liner material 1016. In at least one embodiment of the present disclosure, liner material 1016 comprises a silicone coating on the surface facing adhesive 1015. In the embodiment of wristband label sheet 1000 shown in FIG. 10A, liner material 1016 is bounded by leading edge 1020, trailing edge 1022, side edge 1024, and side edge 1026. Label sheet 1012 may be of any size. In at least one embodiment of label sheet 1012 according to the present disclosure, the outer dimensions of label sheet 1012 are selected to enable label sheet 1012 to fit in a commercially available printing device. For example, in such an embodiment, the outer dimensions of label sheet 1012 may be 8½"×11", 8½"×14", or 210 mm×297 mm.

In at least one embodiment of the present disclosure, label material 1014 comprises perimeter 1019 defining a boundary of label material 1014. In at least one embodiment of the present disclosure, at least a portion of perimeter 1019 is inboard of the boundary formed by leading edge 1020, trailing edge 1022, side edge 1024, and side edge 1026. In at least one embodiment of the present disclosure, perimeter 1019 is coextensive with the boundary formed by leading edge 1020, trailing edge 1022, side edge 1024, and side edge 1026.

In at least one embodiment of the present disclosure, label material 1014 comprises a material suitable for the printing of indicia thereon, such as, for example, paper, polyester, or another polymer material. Indicia may be marked or printed on the top side of label material 1014. For example, the top side of label material 1014 may be exposed to an ink jet printer, a laser print, or another type of printing device capable of applying indicia to the top side of label material 1014. The inks, toners, and/or other printing materials used in the application of indicia to the top side of label material 1014 are selected to be compatible with the printing device used to apply such indicia, the material used for label material 1014, and the intended use of wristband label sheet 1000.

In the embodiment of wristband label sheet 1000 shown in FIG. 10A, label material 1014 comprises a plurality of labels 1018. In at least one embodiment, labels 1018 are die cut in label material 1014. In at least one embodiment of the present disclosure, label material 1014 comprises twenty-four labels 1018, each having dimensions of about 1"×2.5". Other sizes and quantities of labels 1018 are possible.

In at least one embodiment of the present disclosure, wristband 1032 is constructed of a polyester material, although other materials suitable for the intended use of wristband 1032 may be used. In at least one embodiment of the present disclosure, wristband 1032 has dimensions of about 1"×10.75", however wristband 1032 may be of any size that fits on label sheet 1012.

Figure 10B:
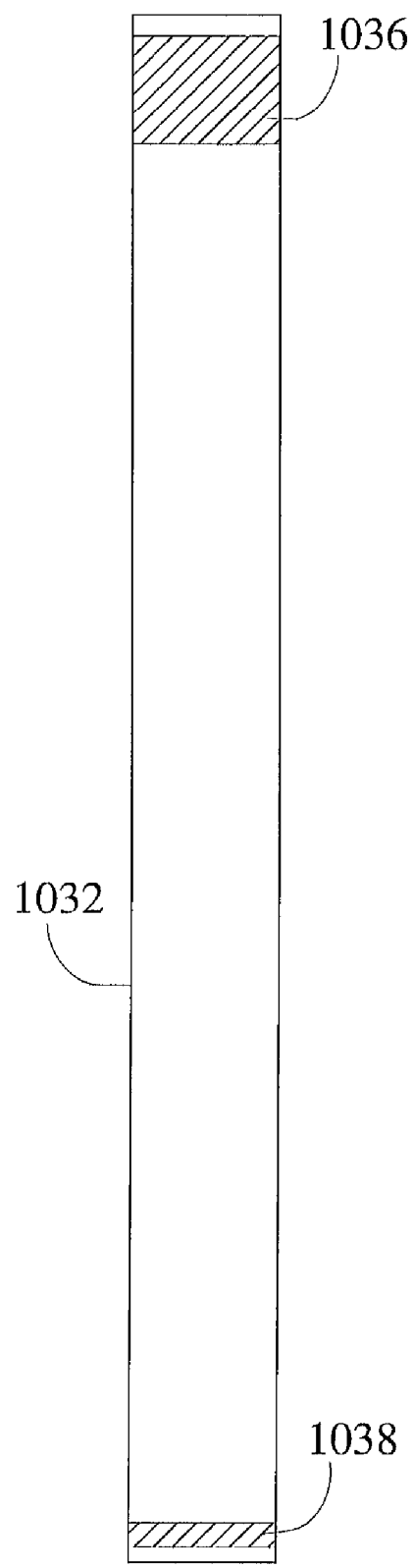
FIG. 10B shows the underside of a wristband according to at least one embodiment of the present disclosure.

FIG. 10B shows the underside of wristband 1032 before attachment to label sheet 1012, according to at least one embodiment of the present disclosure. Shown in FIG. 10B are wristband 1032 comprising adhesive stripe 1036 and adhesive stripe 1038. In at least one embodiment of the present disclosure, adhesive stripes 1036 and 1038 comprise a layer of a repositionable adhesive. In at least one embodiment of the present disclosure, adhesive stripes 1036 and 1038 comprise a layer of a removable adhesive. In at least one embodiment of the present disclosure, adhesive stripes 1036 and 1038 comprise a layer of a pressure sensitive adhesive.

Referring back to FIG. 10A, shown therein are the locations of adhesive stripes 1036, 1038 on the underside of wristband 1032. Adhesive stripe 1036 is interposed between wristband 1032 to label material 1014 and removably adheres wristband 1032 to label material 1014. Adhesive stripe 1038 is interposed between wristband 1032 to label material 1014 and removably adheres wristband 1032 to label material 1014. As discussed hereinafter, adhesive stripes 1036, 1038 are operable to secure wristband 1032 around a subject's wrist after wristband 1032 is removed from label sheet 1012.

Indicia may be marked or printed on the top side of wristband 1032. For example, the top side of wristband 1032 may be exposed to an ink jet printer, a laser print, or another type of printing device capable of applying indicia to the top side of wristband 1032. Indicia may be printed on wristband 1032 before, after, or concurrently with the printing of indicia on label material 1014. The inks, toners, and/or other printing materials used in the application of indicia to the top side of wristband 1032 are selected to be compatible with the printing device used to apply such indicia, the material used for wristband 1032, and the intended use of wristband 1032.

Figure 11:
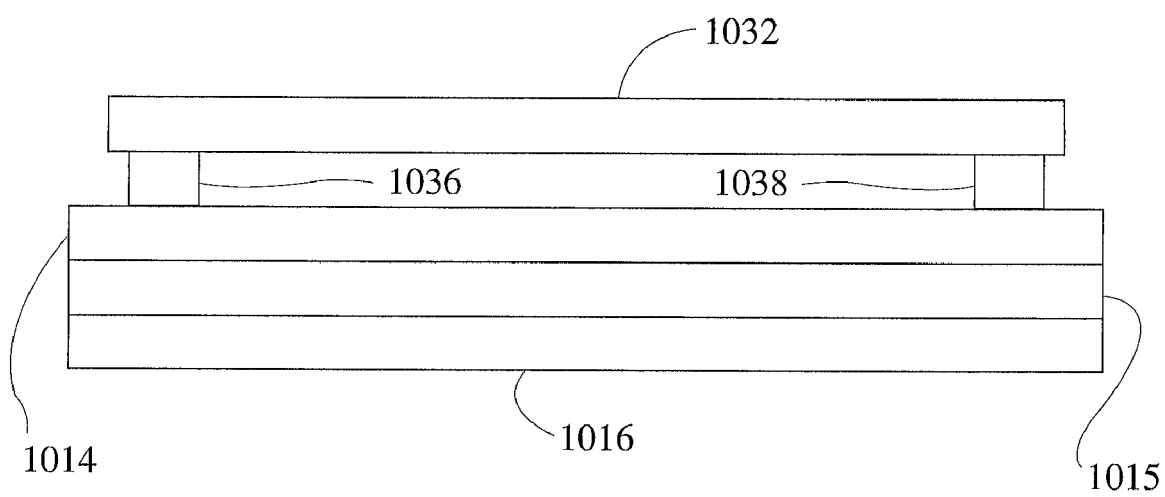
FIG. 11 shows a cross-sectional view of an embodiment of a wristband label sheet according to at least one embodiment of the present disclosure.

FIG. 11 shows a cross-sectional view of the embodiment of wristband label sheet 1000 of FIG. 10A taken on line XI-XI of FIG. 10A, with the proportions enhanced for purposes of clarity. Shown in FIG. 11 are label material 1014, adhesive layer 1015, liner material 1016, wristband 1032, adhesive stripe 1036, and adhesive stripe 1038.

Figure 12:
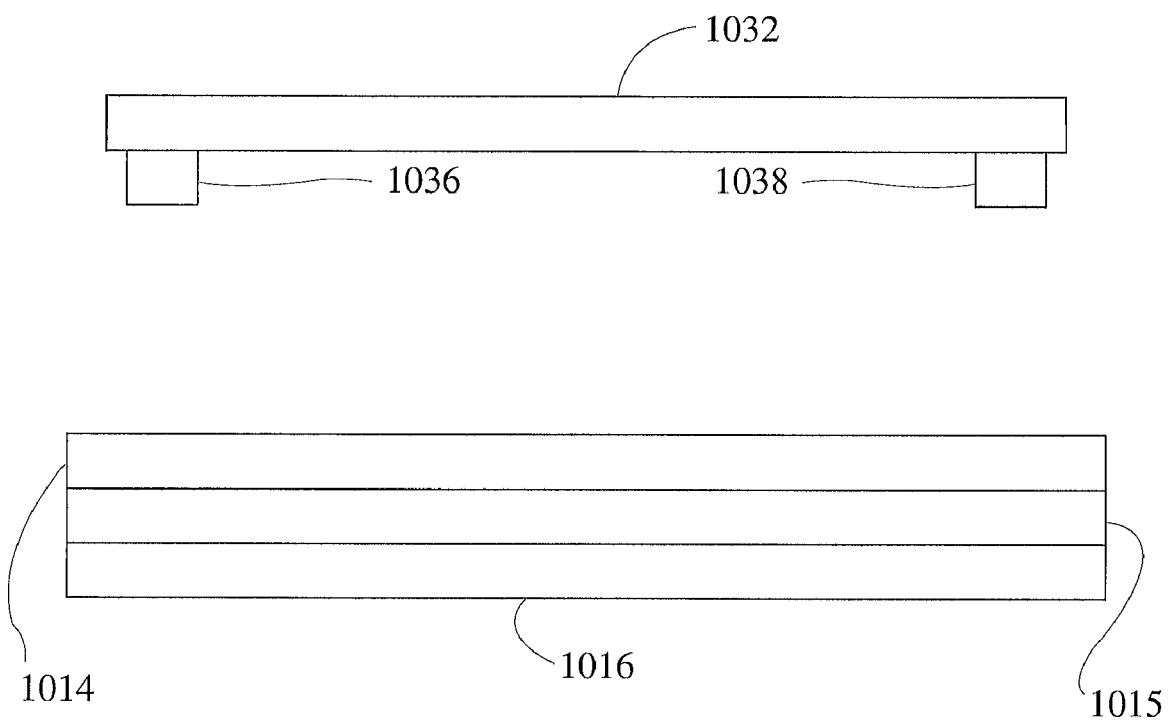
FIG. 12 shows a cross-sectional of an embodiment of a wristband label sheet according to at least one embodiment of the present disclosure.

According to at least one embodiment of the present disclosure, wristband 1032 is removable from label sheet 1012 by grasping wristband 1032 between adhesive stripe 1036 and adhesive stripe 1038 and pulling wristband 1032 away from label sheet 1012. FIG. 12 shows a cross-sectional view of an embodiment of wristband label sheet 1000 according to at least one embodiment of the present disclosure, with the proportions enhanced for purposes of clarity. As shown in FIG. 12, wristband 1032 is separated from label sheet 1012. As shown in FIG. 12, adhesive stripe 1036 and adhesive stripe 1038 have separated from label material 1014. Adhesive stripe 1036 and adhesive stripe 1038 remain adhered to the underside of wristband 1032.

Figure 13A:
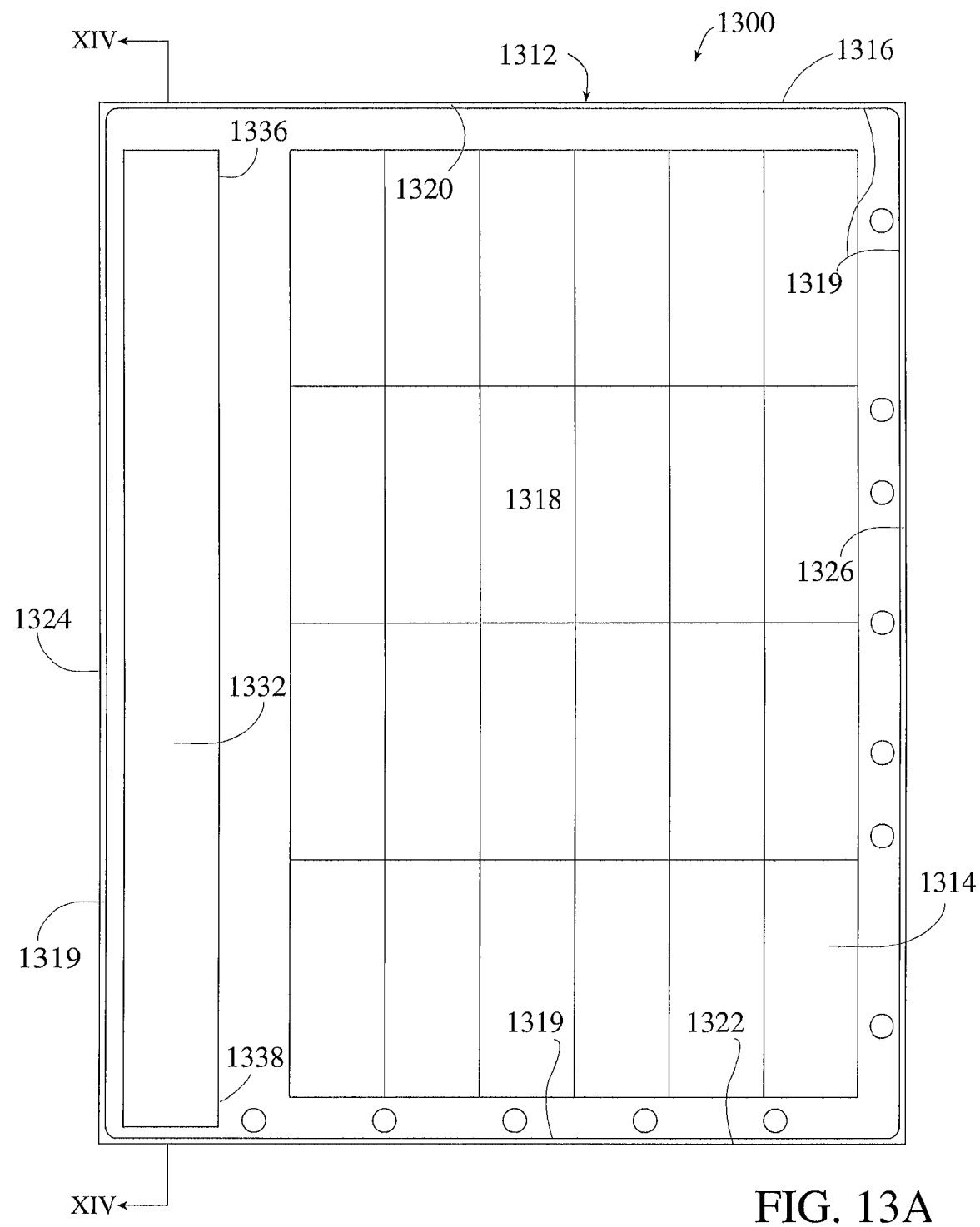
FIG. 13A shows a top view of a wristband label sheet according to at least one embodiment of the present disclosure.

FIG. 13A shows a top view of wristband label sheet 1300 according to at least one embodiment of the present disclosure. Shown in FIG. 13A are label sheet 1312, comprising label material 1314 and liner material 1316. Adhesive 1315 (not shown in FIG. 13A) is interposed between label material 1314 and liner material 1316 and removably adheres label material 1314 to liner material 1316. In at least one embodiment of the present disclosure, liner material 1316 comprises a silicone coating on the surface facing adhesive 1315. In the embodiment of wristband label sheet 1300 shown in FIG. 13A, liner material 1316 is bounded by leading edge 1320, trailing edge 1322, side edge 1324, and side edge 1326. Label sheet 1312 may be of any size. In at least one embodiment of label sheet 1312 according to the present disclosure, the outer dimensions of label sheet 1312 are selected to enable label sheet 1312 to fit in a commercially available printing device. For example, in such an embodiment, the outer dimensions of label sheet 1312 may be 8½"×11", 8½"×14", or 210 mm×297 mm.

In at least one embodiment of the present disclosure, label material 1314 comprises perimeter 1319 defining a boundary of label material 1314. In at least one embodiment of the present disclosure, at least a portion of perimeter 1319 is inboard of the boundary formed by leading edge 1320, trailing edge 1322, side edge 1324, and side edge 1326. In at least one embodiment of the present disclosure, perimeter 1319 is coextensive with the boundary formed by leading edge 1320, trailing edge 1322, side edge 1324, and side edge 1326.

In at least one embodiment of the present disclosure, label material 1314 comprises a material suitable for the printing of indicia thereon, such as, for example, paper, polyester, or another polymer material. Indicia may be marked or printed on the top side of label material 1314. For example, the top side of label material 1314 may be exposed to an ink jet printer, a laser print, or another type of printing device capable of applying indicia to the top side of label material 1314. The inks, toners, and/or other printing materials used in the application of indicia to the top side of label material 1314 are selected to be compatible with the printing device used to apply such indicia, the material used for label material 1314, and the intended use of wristband label sheet 1300.

In the embodiment of wristband label sheet 1300 shown in FIG. 13A, label material 1314 comprises a plurality of labels 1318. In at least one embodiment, labels 1318 are die cut in label material 1314. In at least one embodiment of the present disclosure, label material 1314 comprises twenty-four labels 1318, each having dimensions of about 1"×2.5". Other sizes and quantities of labels 1318 are possible.

In at least one embodiment of the present disclosure, wristband 1332 is constructed of a polyester material, although other materials suitable for the intended use of wristband 1332 may be used. In at least one embodiment of the present disclosure, wristband 1332 has dimensions of about 1"×10.75", however wristband 1332 may be of any size that fits on label sheet 1312.

Figure 13B:
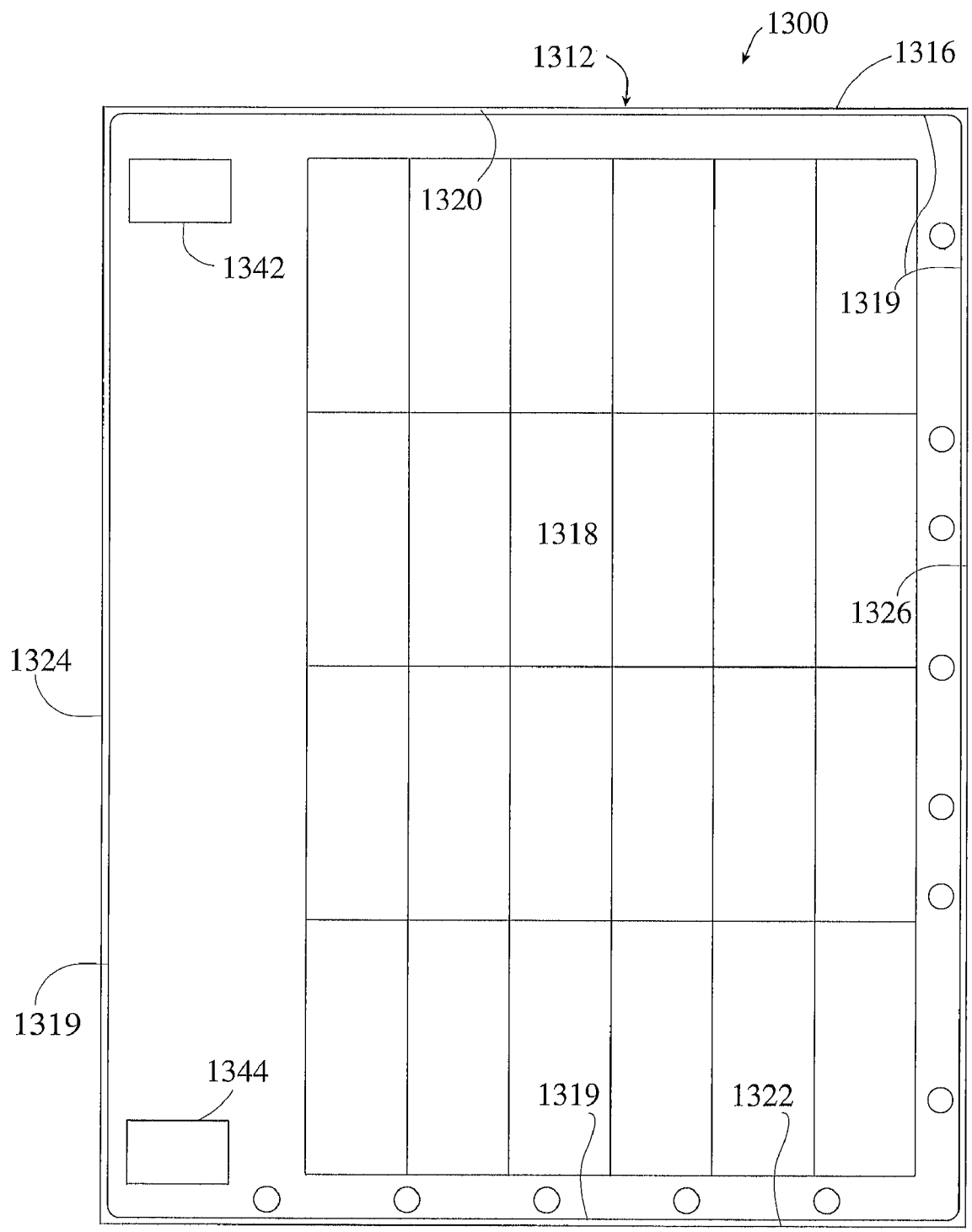
FIG. 13B shows a top view of a label sheet according to at least one embodiment of the present disclosure.

FIG. 13B shows a top view of wristband label sheet 1300 according to at least one embodiment of the present disclosure without the application of wristband 1332. Shown in FIG. 13B are patches 1342 and 1344. In at least one embodiment, patches 1342 and 1344 are die cut in label material 1314.

Referring back to FIG. 13A, shown therein are the locations of adhesive stripes 1336, 1338 on the underside of wristband 1332. Adhesive stripe 1336 is interposed between wristband 1332 and patch 1342 and adheres wristband 1332 to label material 1314. Adhesive stripe 1338 is interposed between wristband 1332 and patch 1344 and adheres wristband 1332 to label material 1314.

Indicia may be marked or printed on the top side of wristband 1332. For example, the top side of wristband 1332 may be exposed to an ink jet printer, a laser print, or another type of printing device capable of applying indicia to the top side of wristband 1332. Indicia may be printed on wristband 1332 before, after, or concurrently with the printing of indicia on label material 1314. The inks, toners, and/or other printing materials used in the application of indicia to the top side of wristband 1332 are selected to be compatible with the printing device used to apply such indicia, the material used for wristband 1332, and the intended use of wristband 1332.

Figure 14:
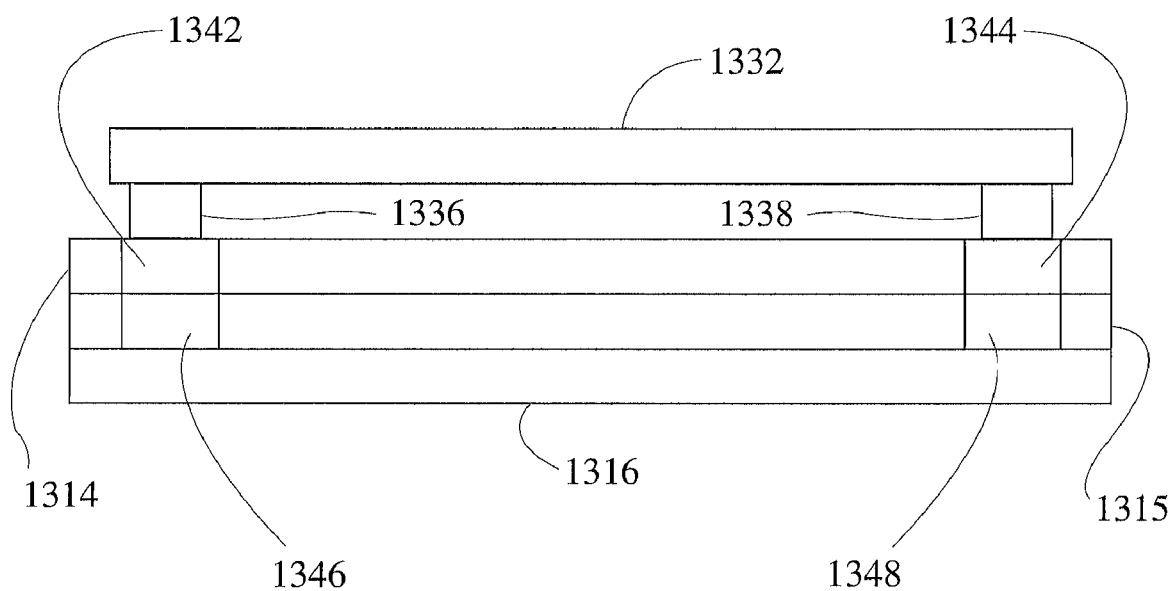
FIG. 14 shows a cross-sectional view of an embodiment of a wristband label sheet according to at least one embodiment of the present disclosure.

FIG. 14 shows a cross-sectional view of the embodiment of wristband label sheet 1300 of 13 FIG. 13A taken on line XIV-XIV of FIG. 13A, with the proportions enhanced for purposes of clarity. Shown in FIG. 14 are label material 1314, adhesive layer 1315, liner material 1316, wristband 1332, adhesive stripe 1336, adhesive stripe 1338, patch 1342, patch 1344, adhesive deposit 1346, and adhesive deposit 1348.

Figure 15:
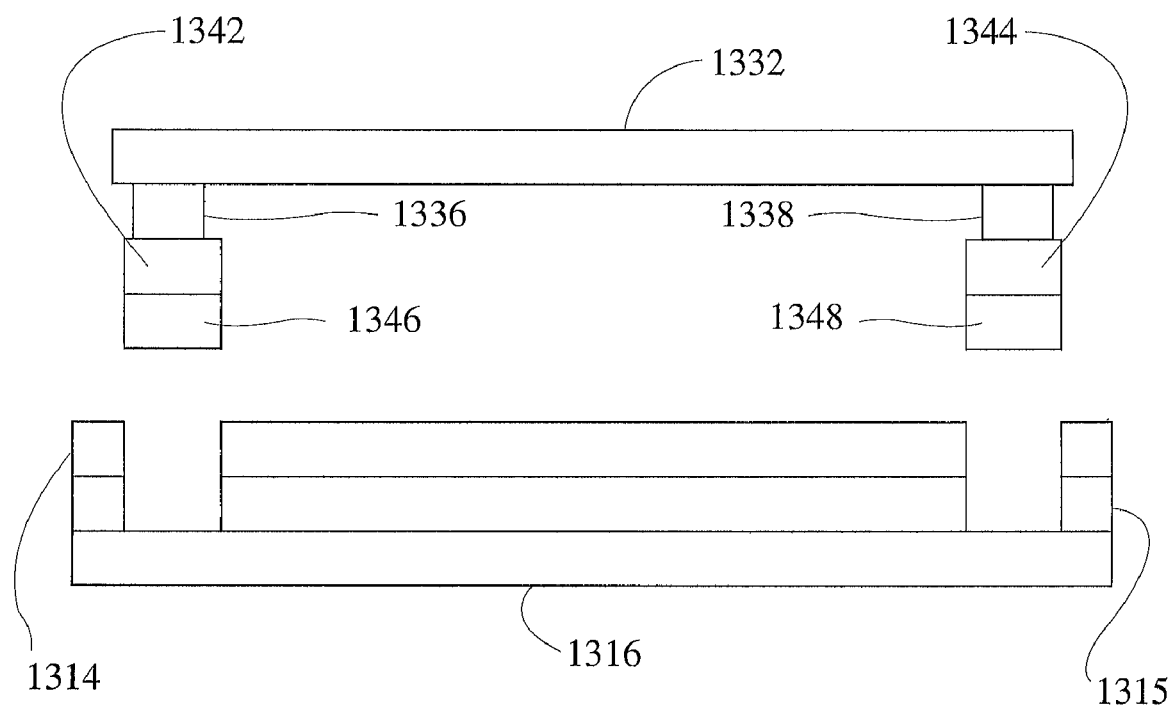
FIG. 15 shows a cross-sectional of an embodiment of a wristband label sheet according to at least one embodiment of the present disclosure.

According to at least one embodiment of the present disclosure, wristband 1332 is removable from label sheet 1312 by grasping wristband 1332 between adhesive stripe 1336 and adhesive stripe 1338 and pulling wristband 1332 away from label sheet 1312. FIG. 15 shows a cross-sectional view of an embodiment of wristband label sheet 1300 according to at least one embodiment of the present disclosure, with the proportions enhanced for purposes of clarity. As shown in FIG. 15, wristband 1332 is separated from label sheet 1312. As shown in FIG. 15, adhesive stripe 1336 and adhesive stripe 1338 remain adhered to the underside of wristband 1332. As shown in FIG. 15, patch 1342 remains adhered to adhesive stripe 1336 and patch 1344 remains adhered to adhesive stripe 1338 after wristband 1332 is separated from label sheet 1312. Adhesive layer 1315 comprises adhesive deposit 1346 and adhesive deposit 1348. As shown in FIG. 15, when wristband 1332 is separated from label sheet 1312 along with adhesive stripe 1336, adhesive stripe 1338, patch 1342, and patch 1344, adhesive deposit 1346 remains adhered to patch 1342 and adhesive deposit 1348 remains adhered to patch 1344.

Figure 16:
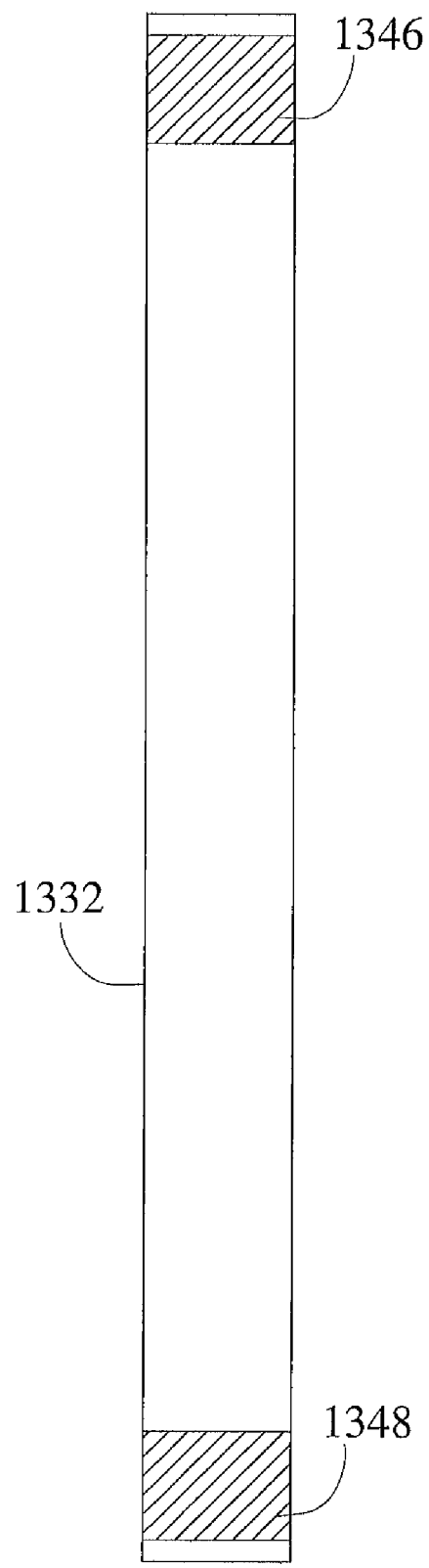
FIG. 16 shows the underside of a wristband according to at least one embodiment of the present disclosure.

FIG. 16 shows the underside of wristband 1332 after separation from label sheet 1312, according to at least one embodiment of the present disclosure. Shown in FIG. 16 are wristband 1332 comprising adhesive deposit 1346 and adhesive deposit 1348. In at least one embodiment of the present disclosure, adhesive deposit 1346 and adhesive deposit 1348 comprise a layer of a repositionable adhesive. In at least one embodiment of the present disclosure, adhesive deposit 1346 and adhesive deposit 1348 comprise a layer of a removable adhesive. In at least one embodiment of the present disclosure, adhesive deposit 1346 and adhesive deposit 1348 comprise a layer of a pressure sensitive adhesive. When wristband 1332 according to an embodiment of the present invention is looped around the wrist of a subject, and the ends of wristband 1332 are adhered together using one or more of adhesive deposits 1346, 1348.

Figure 17A:
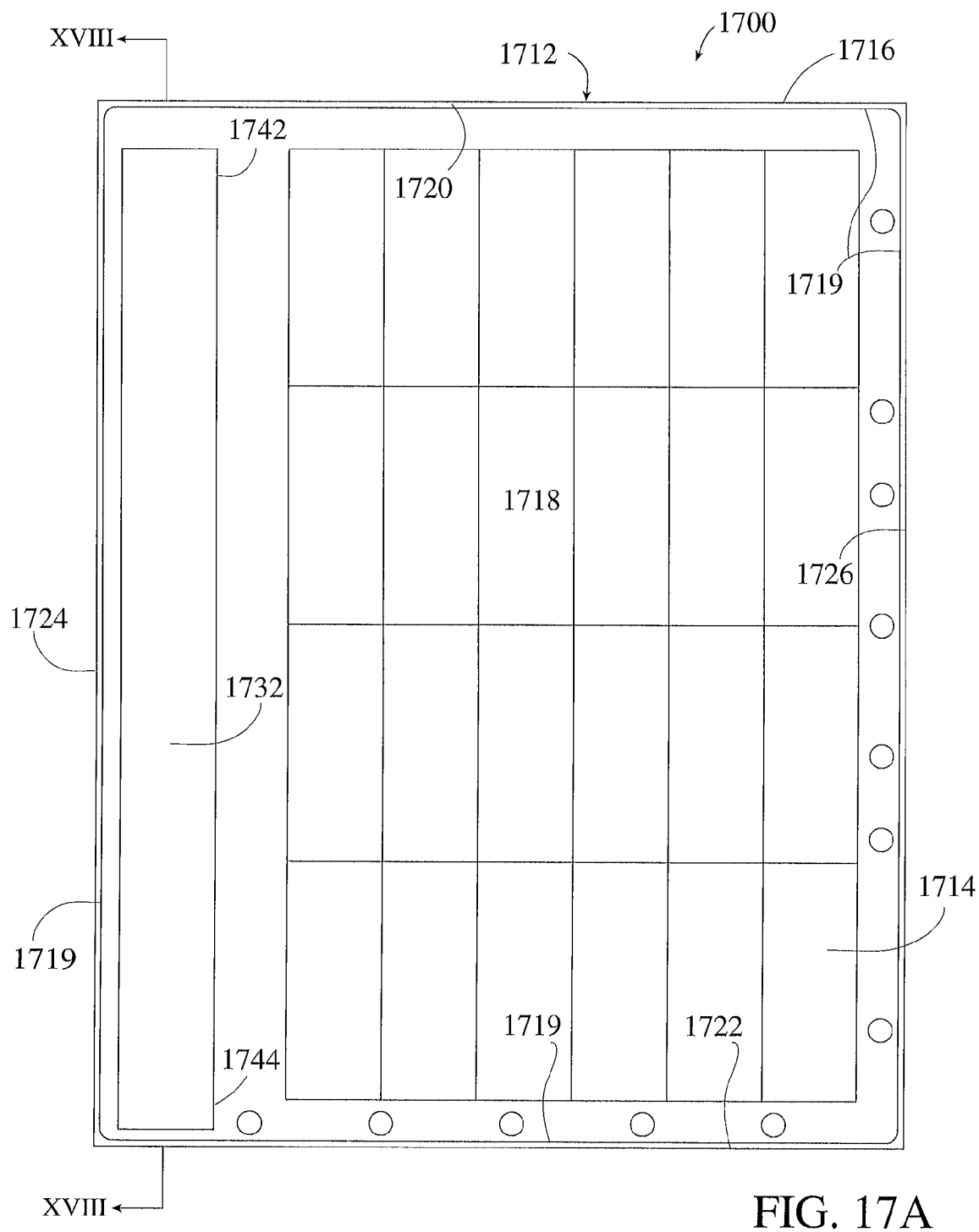
FIG. 17A shows a top view of a wristband label sheet according to at least one embodiment of the present disclosure.

FIG. 17A shows a top view of wristband label sheet 1700 according to at least one embodiment of the present disclosure. Shown in FIG. 17A are label sheet 1712, comprising label material 1714 and liner material 1716. Adhesive 1715 is interposed between label material 1714 and liner material 1716 and removably adheres label material 1714 to liner material 1716. In at least one embodiment of the present disclosure, liner material 1716 comprises a silicone coating on the surface facing adhesive 1715. In the embodiment of wristband label sheet 1700 shown in FIG. 17A, liner material 1716 is bounded by leading edge 1720, trailing edge 1722, side edge 1724, and side edge 1726. Label sheet 1712 may be of any size. In at least one embodiment of label sheet 1712 according to the present disclosure, the outer dimensions of label sheet 1712 are selected to enable label sheet 1712 to fit in a commercially available printing device. For example, in such an embodiment, the outer dimensions of label sheet 1712 may be 8½"×11", 8½"×14", or 210 mm×297 mm.

In at least one embodiment of the present disclosure, label material 1714 comprises perimeter 1719 defining a boundary of label material 1714. In at least one embodiment of the present disclosure, at least a portion of perimeter 1719 is inboard of the boundary formed by leading edge 1720, trailing edge 1722, side edge 1724, and side edge 1726. In at least one embodiment of the present disclosure, perimeter 1719 is coextensive with the boundary formed by leading edge 1720, trailing edge 1722, side edge 1724, and side edge 1726.

In at least one embodiment of the present disclosure, label material 1714 comprises a material suitable for the printing of indicia thereon, such as, for example, paper, polyester, or another polymer material. Indicia may be marked or printed on the top side of label material 1714. For example, the top side of label material 1714 may be exposed to an ink jet printer, a laser print, or another type of printing device capable of applying indicia to the top side of label material 1714. The inks, toners, and/or other printing materials used in the application of indicia to the top side of label material 1714 are selected to be compatible with the printing device used to apply such indicia, the material used for label material 1714, and the intended use of wristband label sheet 1700.

In the embodiment of wristband label sheet 1700 shown in FIG. 17A, label material 1714 comprises a plurality of labels 1718. In at least one embodiment, labels 1718 are die cut in label material 1714. In at least one embodiment of the present disclosure, label material 1714 comprises twenty-four labels 1718, each having dimensions of about 1"×2.5". Other sizes and quantities of labels 1718 are possible.

In at least one embodiment of the present disclosure, wristband 1732 is constructed of a polyester material, although other materials suitable for the intended use of wristband 1732 may be used. In at least one embodiment of the present disclosure, wristband 1732 has dimensions of about 1"×10.75", however wristband 1732 may be of any size that fits on label sheet 1712.

Figure 17B:
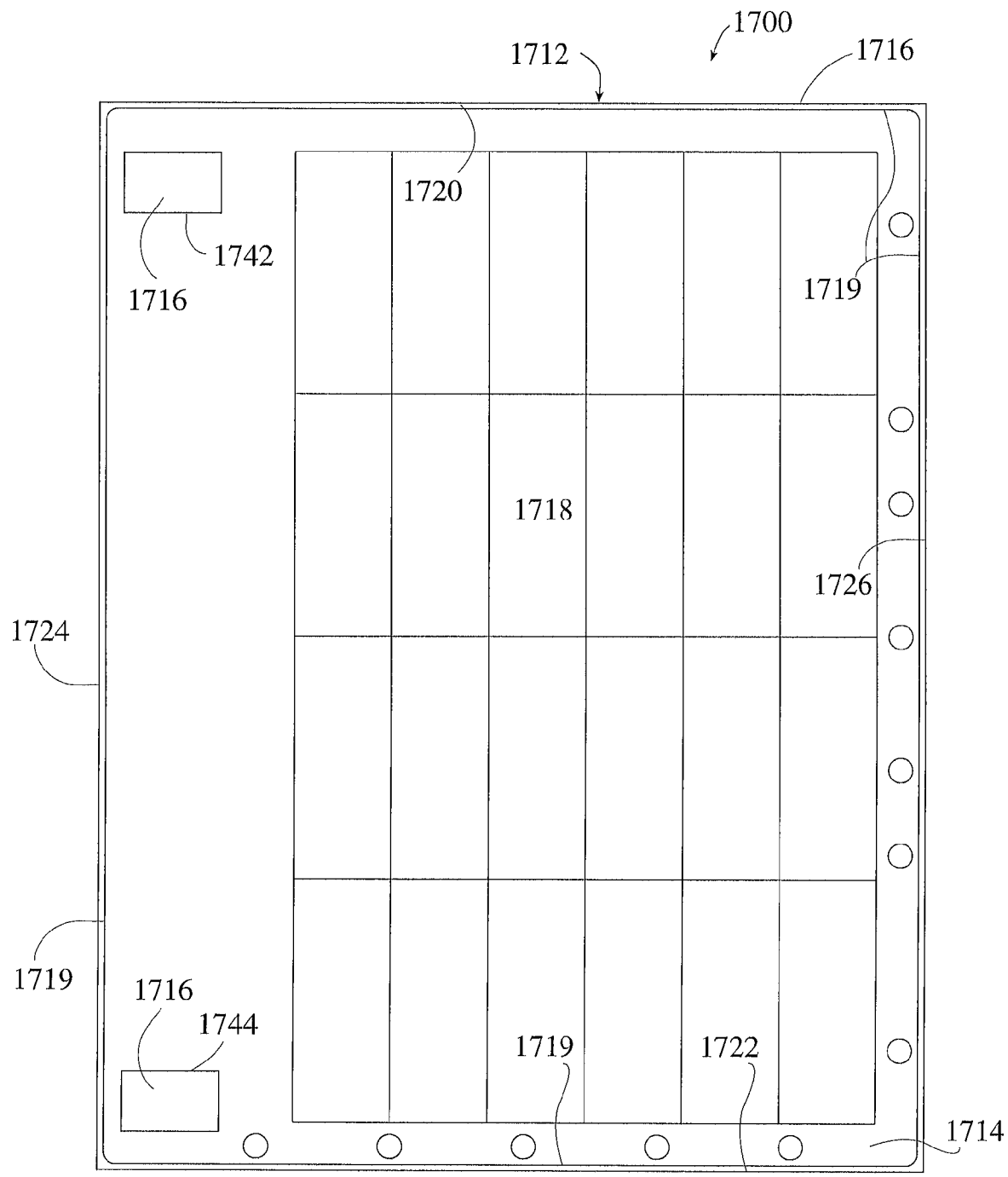
FIG. 17B shows a top view of a label sheet according to at least one embodiment of the present disclosure.

FIG. 17B shows a top view of wristband label sheet 1700 according to at least one embodiment of the present disclosure without the application of wristband 1732. Shown in FIG. 17B are voids 1742 and 1744. In at least one embodiment, voids 1742 and 1744 comprises portions of label material 1714 and adhesive 1715 that have been removed. As shown in FIG. 17B, removal of such portions of label material 1714 exposes liner 1716.

Referring back to FIG. 17A, shown therein are the locations of label material and adhesive voids 1742 and 1744 that are obscured by wristband 1732.

Indicia may be marked or printed on the top side of wristband 1732. For example, the top side of wristband 1732 may be exposed to an ink jet printer, a laser print, or another type of printing device capable of applying indicia to the top side of wristband 1732. Indicia may be printed on wristband 1732 before, after, or concurrently with the printing of indicia on label material 1714. The inks, toners, and/or other printing materials used in the application of indicia to the top side of wristband 1732 are selected to be compatible with the printing device used to apply such indicia, the material used for wristband 1732, and the intended use of wristband 1732.

Figure 18:
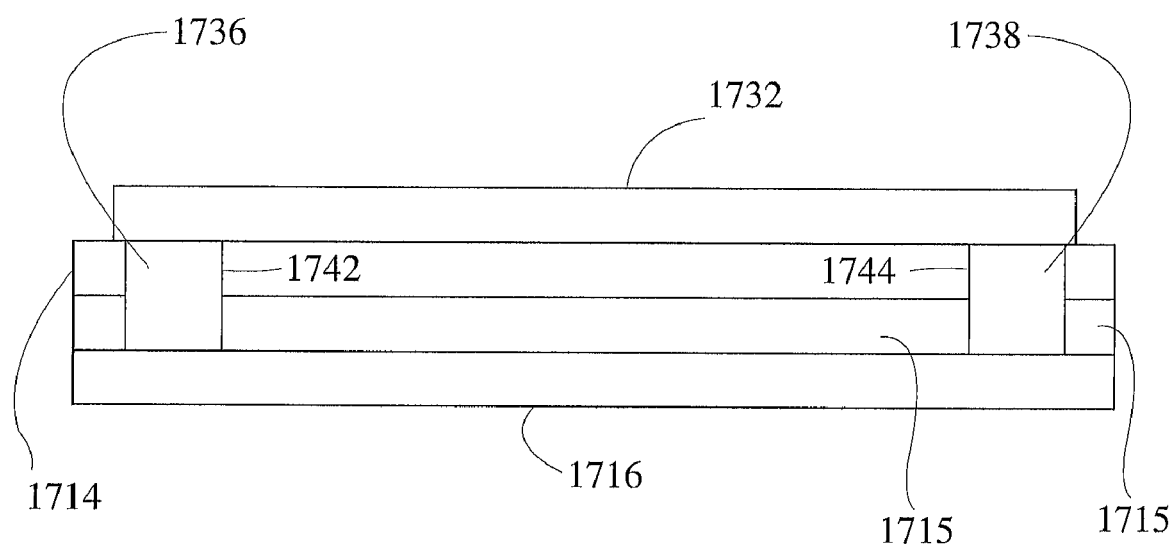
FIG. 18 shows a cross-sectional view of an embodiment of a wristband label sheet according to at least one embodiment of the present disclosure.

FIG. 18 shows a cross-sectional view of the embodiment of wristband label sheet 1700 of 17 FIG. 17A taken on line XVIII-XVIII of FIG. 17A, with the proportions enhanced for purposes of clarity. Shown in FIG. 18 are label material 1714, adhesive layer 1715, liner material 1716, wristband 1732, adhesive stripe 1736, adhesive stripe 1738, void 1742, and void 1744.

Figure 19:
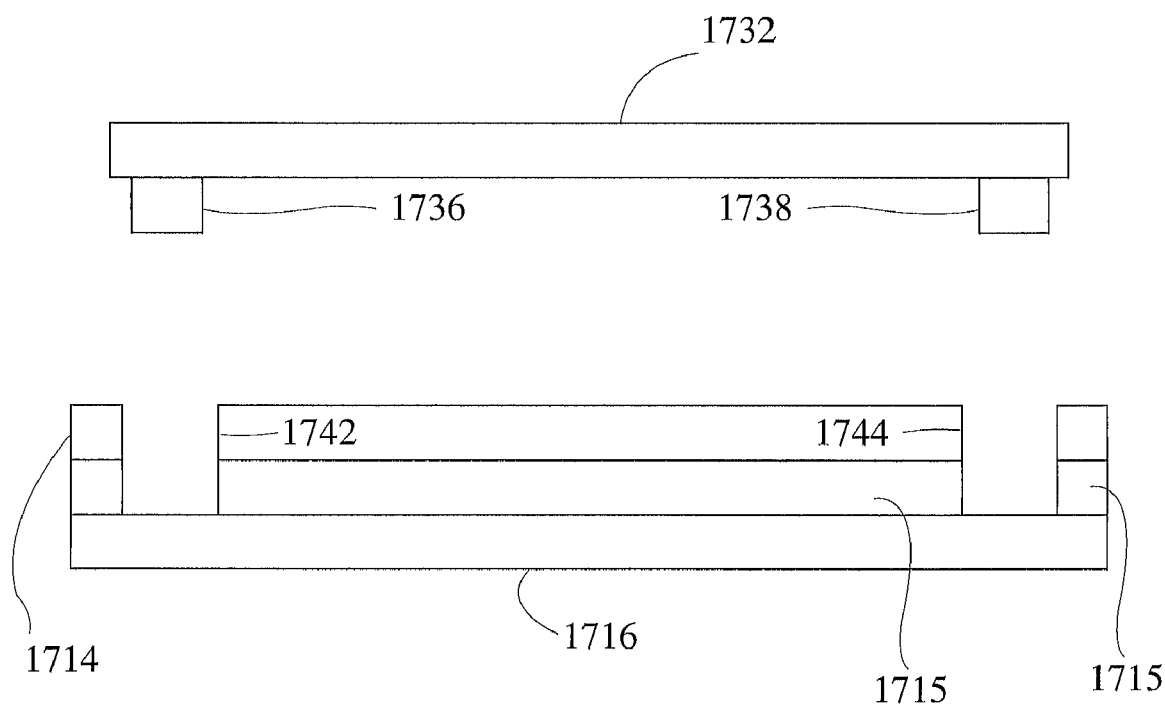
FIG. 19 shows a cross-sectional of an embodiment of a wristband label sheet according to at least one embodiment of the present disclosure.

According to at least one embodiment of the present disclosure, wristband 1732 is removable from label sheet 1712 by grasping wristband 1732 between adhesive stripe 1736 and adhesive stripe 1738 and pulling wristband 1732 away from label sheet 1712. FIG. 19 shows a cross-sectional view of an embodiment of wristband label sheet 1700 according to at least one embodiment of the present disclosure, with the proportions enhanced for purposes of clarity. As shown in FIG. 19, wristband 1732 is separated from label sheet 1712. As shown in FIG. 19, adhesive stripe 1736 and adhesive stripe 1738 remain adhered to the underside of wristband 1732 after wristband 1732 is separated from label sheet 1712.

Figure 20:
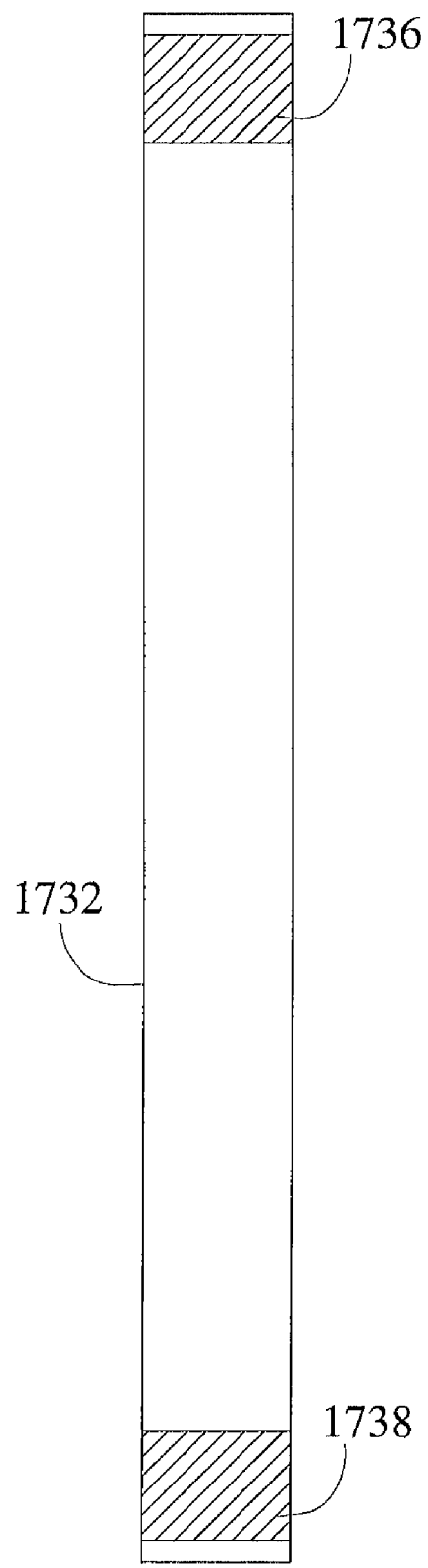
FIG. 20 shows the underside of a wristband according to at least one embodiment of the present disclosure.

FIG. 20 shows the underside of wristband 1732 after separation from label sheet 1712, according to at least one embodiment of the present disclosure. Shown in FIG. 20 are wristband 1732 comprising adhesive stripe 1736 and adhesive stripe 1738. In at least one embodiment of the present disclosure, adhesive stripe 1736 and adhesive stripe 1738 comprises a layer of a repositionable adhesive. In at least one embodiment of the present disclosure, adhesive stripe 1736 and adhesive stripe 1738 comprises a layer of a removable adhesive. In at least one embodiment of the present disclosure, adhesive stripe 1736 and adhesive stripe 1738 comprises a layer of a pressure sensitive adhesive. When wristband 1732 according to an embodiment of the present invention is looped around the wrist of a subject, and the ends of wristband 1732 are adhered together using one or more of adhesive stripe 1736 and adhesive stripe 1738 on wristband 1732.

While this disclosure has been described as having preferred designs, the apparatus and methods according to the present disclosure can be further modified within the scope and spirit of this disclosure. This application is therefore intended to cover any variations, uses, or adaptations of the disclosure using its general principles. For example, the sizes, quantities, and locations of the wristband(s), adhesive stripes, lines of weakness, and/or printed release patches can be varied.

In another example, although the embodiments disclosed herein are disclosed in terms of the application of wristband to a label sheet, embodiments comprising the application of a wristband to another form of sheet material such as, for example, paper or a plastic, are within the scope of the present disclosure.

In yet another example, although the embodiments disclosed herein are disclosed in terms of one wristband to a label sheet, embodiments comprising the application of more than one wristband to a label sheet are within the scope of the present disclosure.

In yet another example, an embodiment of a wristband label sheet according to at least one embodiment of the present disclosure may comprise an RFID inlay on the top side or underside of the wristband.

As a further example, any methods disclosed herein and in the appended claims represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains.

We claim:

1. A printable form comprising:
   a substrate material, said substrate material comprising a leading edge, a trailing edge, and first and second side edges, said substrate material comprising a face ply and a liner ply, said face ply comprising a face ply surface and a second surface opposite said face ply surface, said liner ply removably adhered to said second surface of said face ply;

a wristband, said wristband comprising a leading margin, a trailing margin, first and second side margins, a stub portion, a removeable portion, and a transverse line of weakness between said stub portion and said removeable portion, a top side, and an underside, said underside comprising an underside surface bounded by said leading margin, said trailing margin, and said first and second side margins; and at least one adhesive stripe adhered to said underside surface, at least one of said at least one adhesive stripes releasably bonded to said face ply surface such that said wristband is removably attached to said face ply surface, wherein at least one of said at least one adhesive stripes is adhered to said underside surface on each side of said transverse line of weakness and said removeable portion is separable from said stub portion at said transverse line of weakness, wherein said stub portion is permanently adhered to said face ply surface.

* * * * *